US009127080B2

(12) United States Patent
Adhya

(10) Patent No.: US 9,127,080 B2
(45) Date of Patent: Sep. 8, 2015

(54) PROTEIN-CODING RNA TO CORRECT MITOCHONDRIAL DYSFUNCTION

(75) Inventor: Samit Adhya, West Bengal (IN)

(73) Assignee: Council of Scientific and Industrial Research, New Delhi (IN)

(*) Notice: Subject to any disclaimer, the term of this patent is extended or adjusted under 35 U.S.C. 154(b) by 1001 days.

(21) Appl. No.: 12/584,059

(22) Filed: Aug. 28, 2009

(65) Prior Publication Data

US 2010/0168213 A1 Jul. 1, 2010

(51) Int. Cl.

| | |
|---|---|
| ***C07H 21/04*** | (2006.01) |
| ***C12N 15/63*** | (2006.01) |
| ***C07K 14/47*** | (2006.01) |
| ***A61K 48/00*** | (2006.01) |
| *A61K 31/715* | (2006.01) |

(52) U.S. Cl.

CPC .......... *C07K 14/4707* (2013.01); *A61K 48/005* (2013.01); *A61K 48/0008* (2013.01); *A61K 48/0025* (2013.01); *C07K 2319/07* (2013.01); *C12N 2810/10* (2013.01)

(58) Field of Classification Search

CPC .......... C07K 14/4707; A61K 48/0025; A61K 48/005

See application file for complete search history.

(56) References Cited

U.S. PATENT DOCUMENTS

| | | | | |
|---|---|---|---|---|
| 7,279,326 | B2 * | 10/2007 | Weissig et al. | 435/320.1 |
| 7,361,752 | B2 | 4/2008 | Heidenreich et al. | |
| 2010/0111911 | A1 * | 5/2010 | Guy et al. | 424/93.21 |

OTHER PUBLICATIONS

Taylor, R.W., & Turnbull, D.M.(2005) Mitochondrial DNA mutations in human disease. Nature Rev Genet 6: 389-402.

Wilson, F.H., et al. (2004) A cluster of metabolic defects caused by mutation in a mitochondrial tRNA. Science 306: 1190-1194.

Lowell, B.B. & Shullman, G.L. (2005) Mitochondrial dysfunction and Type 2 diabetes. Science 307: 384-387.

Gottlieb, E., & Tomlinson, I.P.M. (2005) Mitochondrial tumor suppressors: a genetic biochemcial update. Nature Rev Cancer 5:857-867.

Corral-Debrinski M. et al. (1992) Mitochondrial DNA deletions in human brain: regional variability and increase with advanced age. Nature Genet. 2: 324-329.

Kopsidas, G., et al. (1998) An age-associated correlation between cellular bioenergy decline and mtDNA rearrangements in human skeletal muscle. Mut Res 421: 27-36.

Waehler, R., et al (2007) Engineering targeted viral vectors for gene therapy. Nat. Rev., Genet. 8: 573-587.

Klapdor, L., et al, (1997) A low-cost method to analyse footprint patterns J. Neurosci. Meth. 75: 49-54.

Kyriakouli, D.S, et al, (2008) Progress and prospects: gene therapy of mitochondrial DNA disease. Gene Therapy (2008) 15, 1017-1023.

Mahata, B. et al. (2005) Correction of Translational Defects in Patient-derived Mutant Mitochondria by Complex-mediated Import of a Cytoplasmic tRNA. J. Biol. Chem 280:5141-5144.

Collombret J.M., et al (1997) Introduction of Plasmid DNA into isolated mitochondria by electroporation. A novel approach toward gene correction for mitochondrial disorders. J. Biol. Chem, 272: 5342-5347

Vestweber, D., & Schatz, G. (1989) DNA-protein conjugates can enter mitochondria via the protein import pathway. Nature 338: 170-172.

Muratovska A., et al. (2001) Targeting peptide nucleic acid (PNA) oligomers to mitochondria within cells by conjugation to lipophilic cations: implications for mitochondrial DNA replication, expression and disease. Nucl. Acids Res., 29: 1852-1863.

Ojaimi, J., et al. (2002) An algal nucleus-encoded subunit of mitochondrial ATP synthase rescues a defect in the analogous human mitochondrial-encoded subunit. Mol. Biol. Cell 13: 3836-3844.

Bokori-Brown, M. & Holt, I.J. (2006) Expression of algal nuclear ATP synthase subunit 6 in human cells results in protein targeting to mitochondria but no assembly into ATP synthase. Rejuvenation Res. 9: 455-469.

Mukherjee, S. et. al. (2008) Targeted mRNA degradation by complex-mediated delivery of antisense RNAs to intracellular human mitochondria. Hum. Mol. Genet. 17: 1292-1298.

Mukherjee, S., Basu, S., Home, P., Dhar, G., & Adhya, S. (2007) Necessary and sufficient factors for import of tRNA into the kinetoplast-mitochondrion. EMBO Rep., 8: 589-595.

Mahata B., Mukherjee, S., Mishra, S., Bandyopadhyay, A., & Adhya, S. (2006) Functional delivery of a cytosolic tRNA into mutant mitochondria of human cells. Science. 314: 471-474.

Bhattacharya S.N., Chatterjee, S., Goswami, S., Tripathi, G., Dey, S.N., & Adhya, S. (2003) "Ping pong" interactions between mitochondrial tRNA import receptors within a multiprotein complex. Mol. Cell. Biol., 23: 5217-5224.

Goswami, S., Dhar, G., Mukherjee, S., Mahata, B., Chatterjee, S., Home, P., & Adhya, S. (2006) A bi-functional tRNA import receptor from Leishmania mitochondria. Proc. Natl. Acad. Sci. U.S.A., 103: 8354-8359.

Mahapatra, S., Ghosh, S., Bera, S.K., Ghosh, T., Das, A., & Adhya, S. (1998) The O arm of tRNATyr is necessary and sufficient for import into Leishmania mitochondria in vitro. Nucl. Acids Res. 26: 2037-2041.

Anderson, S., et al (1981) Sequence and organization of the human mitochondrial genome. Nature, 290: 457-464.

(Continued)

*Primary Examiner* — Quang Nguyen

(74) *Attorney, Agent, or Firm* — Westman, Champlin & Koehler, P.A.

(57) ABSTRACT

The present invention provides compositions and methods for using correctional RNA, with a proteinaceous carrier, to stimulate respiration of the cells, tissues, organs or the whole organism of normal or diseased subjects. In one embodiment of the invention, the signal-tagged correctional RNA is one or more protein-coding RNAs (pcRNA) that encode one or more of human mitochondrial proteins. The invention specifically provides a broad-spectrum formulation applicable to a wide variety of disorders that are associated with mitochondrial mutations.

9 Claims, 21 Drawing Sheets

(56) References Cited

OTHER PUBLICATIONS

Hutchin, T. & Cortopassi, G. (1995) Proc. Natl. Acad. U.S.A. A mitochondrial DNA clone is associated with increased risk for Alzheimer disease. 92: 6892-6895.

Masucci, J.P., Davidson, M., Koga, Y., Schon, E., and King, M.P., (1995) In Vitro Analysis of Mutations Causing Myoclonus Epilepsy With Ragged-Red fibers in Mitochdrial tRNA Gene: Two Genotypes Produce Similar Phenotypes. Mol. Cell. Biol. 15:2872-2881.

* cited by examiner pcRNA-I pppGGGA*CUGUAGCUCAAUUGGUAGAGCAU*GGAUCCAUGUUCGCCGACCGUUGACUAUUCUCUAC COI
AAACCACAAAGACAUUGGAACACUAUACCUAUUAUUCGGCGCAUGAGCUGGAGUCCUAGGCACAG
CUCUAAGCCUCCUUAUUCGAGCCGAGCUGGGCCAGCCAGGCAACCUUCUAGGUAACGACCACAUC
UACAACGUUAUCGUCACAGCCCAUGCAUUUGUAAUAAUCUUCUUCAUAGUAAUACCCAUCAUAAUC
GGAGGCUUUGGCAACUGACUAGUUCCCCUAAUAAUCGGUGCCCCCGAUAUGGCGUUUCCCCGCAU
AAACAACAUAAGCUUCUGACUCUUACCUCCCUCUCUCCUACUCCUGCUCGCAUCUGCUAUAGUGG
AGGCCGGAGCAGGAACAGGUUGAACAGUCUACCCUCCCUUAGCAGGGAACUACUCCCACCCUGGA
GCCUCCGUAGACCUAACCAUCUUCUCCUUACACCUAGCAGGUGUCUCCUCUAUCUUAGGGGCCAU
CAAUUUCAUCACAACAAUUAUCAAUAUAAAACCCCCUGCCAUAACCCAAUACCAAACGCCCCUCUU
CGUCUGAUCCGUCCUAAUCACAGCAGUCCUACUUCUCCUAUCUCUCCCAGUCCUAGCUGCUGGCA
UCACUAUACUACUAACAGACCGCAACCUCAACACCACCUUCUUCGACCCCGCCGGAGGAGGAGAC
CCCAUUCUAUACCAACACCUAUUCUGAUUUUUCGGUCACCCUGAAGUUUAUAUUCUUAUCCUACCA
GGCUUCGGAAUAAUCUCCCAUAUUGUAACUUACUACUCCGGAAAAAAAGAACCAUUUGGAUACAU
AGGUAUGGUCUGAGCUAUGAUAUCAAUUGGCUUCCUAGGGUUUAUCGUGUGAGCACACCAUAUAU COII
UUACAGUAGGAAUAGACGUAGACACACGAGCAUAUUUCACCUCCGCUACCAUAAUCAUCGCUAUC
CCCACCGGCGUCAAAGUAUUUAGCUGACUCGCCACACUCCACGGAAGCAAUAUGAAAUGAUCUGC
UGCAGUGCUCUGAGCCCUAGGAUUCAUCUUUCUUUUCACCGUAGGUGGCCUGACUGGCAUUGUAU
UAGCAAACUCAUCACUAGACAUCGUACUACACGACACGUACUACGUUGUAGCCCACUUCCACUAU
GUCCUAUCAAUAGGAGCUGUAUUUGCCAUCAUAGGAGGCUUCAUUCACUGAUUUCCCCUAUUCUC
AGGCUACACCCUAGACCAAACCUACGCCAAAAUCCAUUUCACUAUCAUAUUCAUCGGCGUAAAUC
UAACUUUCUUCCCACAACACUUUCUCGGCCUAUCCGGAAUGCCCCGACGUUACUCGGACUACCCC ATP8
GAUGCAUACACCACAUGAAACAUCCUAUCAUCUGUAGGCUCAUUCAUUUCUCUAACAGCAGUAAU ATP6
AUUAAUAAUUUUCAUGAUUUGAGAAGCCUUCGCUUCGAAGCGAAAAGUCCUAAUAGUAGAAGAAC
CCUCCAUAAACCUGGAGUGACUAUAUGGAUGCCCCCCACCCUACCACACAUUCGAAGAACCCGUA
UACAUAAAAUCUAGACAAAAAAGGAAGGAAUCGAACCCCCCAAAGCUGGUUUCAAGCCAACCCCA
UGGCCUCCAUGACUUUUUCAAAAAGGUAUUAGAAAAACCAUUUCAUAACUUUGUCAAAGUUAAAU
UAUAGGCUAAAUCCUAUAUAUCUUAAUGGCACAUGCAGCGCAAGUAGGUCUACAAGACGCUACUU COIII
CCCCUAUCAUAGAAGAGCUUAUCACCUUUCAUGAUCACGCCCUCAUAAUCA

| | |
|---|---|
| [dashed box] | START CODONS |
| [box] | STOP CODONS |
| *XXX* | SIGNAL TAGS |
| **XXX** | INTERGENIC SPACER, tRNA genes and linkers |

FIG. 3A

UUUUCCUUAUCUGCUUCCUAGUCCUGUAUGCCCUUUUCCUAACACUCACAACAAAACUAACUAAUA
CUAACAUCUCAGACGCUCAGGAAAUAGAAACCGUCUGAACUAUCCUGCCCGCCAUCAUCCUAGUC
CUCAUCGCCCUCCCAUCCCUACGCAUCCUUUACAUAACAGACGAGGUCAACGAUCCCUCCCUUAC
CAUCAAAUCAAUUGGCCACCAAUGGUACUGAACCUACGAGUACACCGACUACGGCGGACUAAUCU
UCAACUCCUACAUACUUCCCCCAUUAUUCCUAGAACCAGGCGACCUGCGACUCCUUGACGUUGAC
AAUCGAGUAGUACUCCCGAUUGAAGCCCCCAUUCGUAUAAUAAUUACAUCACAAGACGUCUUGCA
CUCAUGAGCUGUCCCCACAUUAGGCUUAAAAACAGAUGCAAUUCCCGGACGUCUAAACCAAACCA
CUUUCACCGCUACACGACCGGGGGUAUACUACGGUCAAUGCUCUGAAAUCUGUGGAGCAAACCAC
AGUUUCAUGCCCAUCGUCCUAGAAUUAAUUCCCCUAAAAAUCUUUGAAAUAGGGCCCGUAUUUAC
CCUAUAGCACCCCCUCUACCCCCUCUAGAGCCCACUGUAAAGCUAACUUAGCAUUAACCUUUUAA
GUUAAAGAUUAAGAGAACCAACACCUCUUUACAGUGAAAUGCCCCAACUAAAUACUACCGUAUGG
CCCACCAUAAUUACCCCCAUACUCCUUACACUAUUCCUCAUCACCCAACUAAAAAUAUUAAACACA
AACUACCACCUACCUCCCUCACCAAAGCCCAUAAAAAUAAAAAAUUAUAACAAACCCUGAGAACCA
AAAUGAACGAAAAUCUGUUCGCUUCAUUCAUUGCCCCCACAAUCCUAGGCCUACCCGCCGCAGUA
CUGAUCAUUCUAUUUCCCCCUCUAUUGAUCCCCACCUCCAAAUAUCUCAUCAACAACCGACUAAUC
ACCACCCAACAAUGACUAAUCAAACUAACCUCAAAACAAAUGAUAACCAUACACAACACUAAAGGA
CGAACCUGAUCUCUUAUACUAGUAUCCUUAAUCAUUUUUAUUGCCACAACUAACCUCCUCGGACUC
CUGCCUCACUCAUUUACACCAACCACCCAACUAUCUAUAAACCUAGCCAUGGCCAUCCCCUUAUGA
GCGGGCACAGUGAUUAUAGGCUUUCGCUCUAAGAUUAAAAAUGCCCUAGCCCACUUCUUACCACA
AGGCACACCUACACCCCUUAUCCCCAUACUAGUUAUUAUCGAAACCAUCAGCCUACUCAUUCAACC
AAUAGCCCUGGCCGUACGCCUAACCGCUAACAUUACUGCAGGCCACCUACUCAUGCACCUAAUUG
GAAGCGCCACCCUAGCAAUAUCAACCAUUAACCUUCCCUCUACACUUAUCAUCUUCACAAUUCUAA
UUCUACUGACUAUCCUAGAAAUCGCUGUCGCCUUAAUCCAAGCCUACGUUUUCACACUUCUAGUA
AGCCUCUACCUGCACGACAACACAUAAUGACCCACCAAUCACAUGCCUAUCAUAUAGUAAAACCCA
GCCCAUGACCCCUAACAGGGGCCCUCUCAGCCCUCCUAAUGACCUCCGGCCUAGCCAUGUGAUUU
CACUUCCACUCCAUAACGCUCCUCAUACUAGGCCUACUAACCAACACACUAACCAUAUACCAAUGA
UGGCGCGAUGUAACACGAGAAAGCACAUACCAAGGCCACCACACACCACCUGUCCAAAAAGGCCU
UCGAUACGGGAUAAUCCUAUUUAUUACCUCAGAAGUUUUUUUCUUCGCAGGAUUUUUCUGAGCCU
UUUACCACUCCAGCCUAGCCCCUACCCCCCAAUUAGGAGGGCACUGGCCCCCAACAGGCAUCACC
CCGCUAAAUCCCCUAGAAGUCCCACUCCUAAACACAUCCGUAUUACUCGCAUCAGGAGUAUCAAU
CACCUGAGCUCACCAUAGUCUAAUAGAAAACAACCGAAACCAAAUAAU

FIG. 3A continued

UCAAGCACUGCUUAUUACAAUUUUACUGGGUCUCUAUUUUACCCUCCUA
CAAGCCUCAGAGUACUUCGAGUCUCCCUUCACCAUUUCCGACGGCAUCU
ACGGCUCAACAUUUUUUGUAGCCACAGGCUUCCACGGACUUCACGUCAU
UAUUGGCUCAACUUUCCUCACUAUCUGCUUCAUCCGCCAACUAAUAUUU
CACUUUACAUCCAAACAUCACUUUGGCUUCGAAGCCGCCGCCUGAUACU
GGCAUUUUGUAGAUGUGGUUUGACUAUUUCUGUAUGUCUCCAUCUAUUG
AUGAGGGUCUUGGAUCCGC

FIG. 3A continued pcRNA-2 pppGGGA*CUGUAGCUCAAUUGGUAGAGCAUGGAUCC*AUGACCCACCAAUCACAUGCCUAUCAUAUA
GUAAAACCCAGCCCAUGACCCCUAACAGGGGCCCUCUCAGCCCUCCUAAUGACCUCCGGCCUAGC
CAUGUGAUUUCACUUCCACUCCAUAACGCUCCUCAUACUAGGCCUACUAACCAACACACUAACCAU
AUACCAAUGAUGGCGCGAUGUAACACGAGAAAGCACAUACCAAGGCCACCACACACCACCUGUCC
AAAAAGGCCUUCGAUACGGGAUAAUCCUAUUUAUUACCUCAGAAGUUUUUUUCUUCGCAGGAUUU
UUCUGAGCCUUUUACCACUCCAGCCUAGCCCCUACCCCCCAAUUAGGAGGGCACUGGCCCCCAAC
AGGCAUCACCCCGCUAAAUCCCCUAGAAGUCCCACUCCUAAACACAUCCGUAUUACUCGCAUCAG                 ND3
GAGUAUCAAUCACCUGAGCUCACCAUAGUCUAAUAGAAAACAACCGAAACCAAAUAAUUCAAGCA
CUGCUUAUUACAAUUUUACUGGGUCUCUAUUUUACCCUCCUACAAGCCUCAGAGUACUUCGAGUC
UCCCUUCACCAUUUCCGACGGCAUCUACGGCUCAACAUUUUUUGUAGCCACAGGCUUCCACGGAC                 ND4L
UUCACGUCAUUAUUGGCUCAACUUUCCUCACUAUCUGCUUCAUCCGCCAACUAAUAUUUCACUUUA                 ND4
CAUCCAAACAUCACUUUGGCUUCGAAGCCGCCGCCUGAUACUGGCAUUUUGUAGAUGUGGUUUGA
CUAUUUCUGUAUGUCUCCAUCUAUUGAUGAGGGUCUUACUCUUUUAGUAUAAAUAGUACCGUUAA
CUUCCAAUUAACUAGUUUUGACAACAUUCAAAAAAGAGUAAUAAACUUCGCCUUAAUUUUAAUAAU
CAACACCCUCCUAGCCUUACUACUAAUAAUUAUUACAUUUUGACUACCACAACUCAACGGCUACAU
AGAAAAAUCCACCCCUUACGAGUGCGGCUUCGACCCUAUAUCCCCCGCCCGCGUCCCUUUCUCCA
UAAAAUUCUUCUUAGUAGCUAUUACCUUCUUAUUAUUUGAUCUAGAAAUUGCCCUCCUUUUACCCC
UACCAUGAGCCCUACAAACAACUAACCUGCCACUAAUAGUUAUGUCAUCCCUCUUAUUAAUCAUCA
UCCUAGCCCUAAGUCUGGCCUAUGAGUGACUACAAAAAGGAUUAGACUGAACCGAAUUGGUAUAU
AGUUUAAACAAAACGAAUGAUUUCGACUCAUUAAAUUAUGAUAAUCAUAUUUACCAAAUGCCCCUC
AUUUACAUAAAUAUUAUACUAGCAUUUACCAUCUCACUUCUAGGAAUACUAGUAUAUCGCUCACAC
CUCAUAUCCUCCCUACUAUGCCUAGAAGGAAUAAUACUAUCGCUGUUCAUUAUAGCUACUCUCAU
AACCCUCAACACCCACUCCCUCUUAGCCAAUAUUGUGCCUAUUGCCAUACUAGUCUUUGCCGCCU                    ND5
GCGAAGCAGCGGUGGGCCUAGCCCUACUAGUCUCAAUCUCCAACACAUAUGGCCUAGACUACGUA
CAUAACCUAAACCUACUCCAAUGCUAAAACUAAUCGUCCCAACAAUUAUAUUACUACCACUGACAU
GACUUUCCAAAAAACACAUAAUUUGAAUCAACACAACCACCCACAGCCUAAUUAUUAGCAUCAUCC
CUCUACUAUUUUUUAACCAAAUCAACAACAACCUAUUUAGCUGUUCCCCAACCUUUUCCUCCGACC
CCCUAACAACCCCCCUCCUAAUACUAACUACCUGACUCCUACCCCUCACAAUCAUGGCAAGCCAAC
GCCACUUAUCCAGUGAACCACUAUCACGAAAAAAACUCUACCUCUCUAUACUAAUCUCCCUACAAA
UCUCCUUAAUUAUAACAUUCACAGCCACAGAACUAAUCAUAUUUUAUAUCUUCUUCGAAACCACAC
                          UUAUCCCCACCUUGGCUAUCAUCACCCGAUGAGGCAACCAGC

FIG. 3B

CAGAACGCCUGAACGCAGGCACAUACUUCCUAUUCUACACCCUAGUAGG
CUCCCUUCCCCUACUCAUCGCACUAAUUUACACUCACAACACCCUAGGCUCACUAAACAUUCUACU
ACUCACUCUCACUGCCCAAGAACUAUCAAACUCCUGAGCCAACAACUUAAUAUGACUAGCUUACAC
AAUAGCUUUUAUAGUAAAGAUACCUCUUUACGGACUCCACUUAUGACUCCCUAAAGCCCAUGUCG
AAGCCCCCAUCGCUGGGUCAAUAGUACUUGCCGCAGUACUCUUAAAACUAGGCGGCUAUGGUAUA
AUACGCCUCACACUCAUUCUCAACCCCCUGACAAAACACAUAGCCUACCCCUUCCUUGUACUAUCC
CUAUGAGGCAUAAUUAUAACAAGCUCCAUCUGCCUACGACAAACAGACCUAAAAUCGCUCAUUGC
AUACUCUUCAAUCAGCCACAUAGCCCUCGUAGUAACAGCCAUUCUCAUCCAAACCCCCUGAAGCU
UCACCGGCGCAGUCAUUCUCAUAAUCGCCCACGGGCUUACAUCCUCAUUACUAUUCUGCCUAGCA
AACUCAAACUACGAACGCACUCACAGUCGCAUCAUAAUCCUCUCUCAAGGACUUCAAACUCUACUC
CCACUAAUAGCUUUUUGAUGACUUCUAGCAAGCCUCGCUAACCUCGCCUUACCCCCCACUAUUAA
CCUACUGGGAGAACUCUCUGUGCUAGUAACCACGUUCUCCUGAUCAAAUAUCACUCUCCUACUUA
CAGGACUCAACAUACUAGUCACAGCCCUAUACUCCCUCUACAUAUUUACCACAACACAAUGGGGC
UCACUCACCCACCACAUUAACAACAUAAAACCCUCAUUCACACGAGAAAACACCCUCAUGUUCAUA
CACCUAUCCCCCAUUCUCCUCCUAUCCCUCAACCCCGACAUCAUUACCGGGUUUUCCUCUU**GUAAA
UAUAGUUUAACCAAAACAUCAGAUUGUGAAUCUGACAACAGAGGCUUACGACCCCUUAUUUACCG
AGAAAGCUCACAAGAACUGCUAACUCAUGCCCCCAUGUCUAACAACAUGGCUUUCUCAACUUUUA
AAGGAUAACAGCUAUCCAUUGGUCUUAGGCCCCAAAAAUUUUGGUGCAACUCCAAAUAAAAGUA**A
UAACCAUGCACACUACUAUAACCACCCUAACCCUGACUUCCCUAAUUCCCCCCAUCCUUACCACCC
UCGUUAACCCUAACAAAAAAAACUCAUACCCCCAUUAUGUAAAAUCCAUUGUCGCAUCCACCUUUA
UUAUCAGUCUCUUCCCCACAACAAUAUUCAUGUGCCUAGACCAAGAAGUUAUUAUCUCGAACUGA
CACUGAGCCACAACCCAAACAACCCAGCUCUCCCUAAGCUUCAAACUAGACUACUUCUCCAUAAUA
UUCAUCCCUGUAGCAUUGUUCGUUACAUGGUCCAUCAUAGAAUUCUCACUGUGAUAUAUAAACUC
AGACCCAAACAUUAAUCAGUUCUUCAAAUAUCUACUCAUCUUCCUAAUUACCAUACUAAUCUUAGU
UACCGCUAACAACCUAUUCCAACUGUUCAUCGGCUGAGAGGGCGUAGGAAUUAUAUCCUUCUUGC
UCAUCAGUUGAUGAUACGCCCGAGCAGAUGCCAACACAGCAGCCAUUCAAGCAAUCCUAUACAAC
CGUAUCGGCGAUAUCGGUUUCAUCCUCGCCUUAGCAUGAUUUAUCCUACACUCCAACUCAUGAGA
CCCACAACAAAUAGCCCUUCUAAACGCUAAUCCAAGCCUCACCCCACUACUAGGCCUCCUCCUAGC
AGCAGCAGGCAAAUCAGCCCAAUUAGGUCUCCACCCCUGACUCCCCUCAGCCAUAGAAGGCCCCA
CCCCAGUCUCAGCCCUACUCCACUCAAGCACUAUAGUUGUAGCAGGAAUCUUCUUACUCAUCCGC
UUCCACCCCCUAGCAGAAAAUAGCCCACUAAUCCAAACUCUAACACUAUGCUUAGGCGCUAUCA

FIG. 3B continued

CCACUCUGUUCGCAGCAGUCUGCGCCCUUACACAAAAUGACAUCAAAAA
AAUCGUAGCCUUCUCCACUUCAAGUCAACUAGGACUCAUAAUAGUUACAAUCGGCAUCAACCAAC
CACACCUAGCAUUCCUGCACAUCUGUACCCACGCCUUCUUCAAAGCCAUACUAUUUAUGUGCUCC
GGGUCCAUCAUCCACAACCUUAACAAUGAACAAGAUAUUCGAAAAAUAGGAGGACUACUCAAAAC
CAUACCUCUCACUUCAACCUCCCUCACCAUUGGCAGCCUAGCAUUAGCAGGAAUACCUUUCCUCA
CAGGUUUCUACUCCAAAGACCACAUCAUCGAAACCGCAAACAUAUCAUACACAAACGCCUGAGCC
CUAUCUAUUACUCUCAUCGCUACCUCCCUGACAAGCGCCUAUAGCACUCGAAUAAUUCUUCUCACC
CUAACAGGUCAACCUCGCUUCCCCACCCUUACUAACAUUAACGAAAAUAACCCCACCCUACUAAAC
CCCAUUAAACGCCUGGCAGCCGGAAGCCUAUUCGCAGGAUUUCUCAUUACUAACAACAUUUCCCC
CGCAUCCCCCUUCCAAACAACAAUCCCCCUCUACCUAAAACUCACAGCCCUCGCUGUCACUUUCCU
AGGACUUCUAACAGCCCUAGACCUCAACUACCUAACCAACAAACUUAAAAUAAAAUCCCCACUAUG
CACAUUUUAUUUCUCCAACAUACUCGGAUUCUACCCUAGCAUCACACACCGCACAAUCCCCUAUCU
AGGCCUUCUUACGAGCCAAAACCUGCCCCUACUCCUCCUAGACCUAACCUGACUAGAAAAGCUAU
UACCUAAAACAAUUUCACAGCACCAAAUCUCCACCUCCAUCAUCACCUCAACCCAAAAAGGCAUAA
UUAAACUUUACUUCCUCUCUUUCUUCUUCCCACUCAUCCUAACCCUACUCCUAAUCACAUAACCUA
UUCCCCCGAGCAAUCUCAAUUACAAUAUAUACACCAACAAACAAUGUUCAACCAGUAACUACUACU
AAUCAACGCCCAUAAUCAUACAAAGCCCCCGCACCAAUAGGAUCCUCCCGAAUCAACCCUGACCC
CUCUCCUUCAUAAAUUAUUCAGCUUCCUACACUAUUAAAGUUUACCACAACCACCACCCCAUCAUA
CUCUUUCACCCACAGCACCAAUCCUACCUCCAUCGCUAACCCCACUAAAACACUCACCAAGACCUC
AACCCCUGACCCCCAUGCCUCAGGAUACUCCUCAAUAGCCAUCGCUGUAGUAUCCAAAGACAA
CCAUCAUUCCCCCUAAAUAAAUUAAAAAAACUAUUAAACCCAUAUAACCUCCCCCAAAAUUCAGAA
UAAUAACACACCCGACCACACCGCUAACAAUCAAUACUAAACCCCCAUAAAUAGGAGAAGGCUUA
GAAGAAAACCCCACAAACCCCAUUACUAAACCCACACUCAACAGAAACAAAGCAUACAUCAUUAUU
CUCGCACGGACUACAACCACGACCAAUGAUAUGAAAAACCAUCGUUGUAUUUCAACUACAAGAAC
ACCAAUGACCCCAAUACGCAAAACUAACCCCCUAAUAAAAUUAAUUAACCACUCAUUCAUCGACCU
CCCCACCCCAUCCAACAUCUCCGCAUGAUGAAACUUCGGCUCACUCCUUGGCGCCUGCCUGAUCC
UCCAAAUCACCACAGGACUAUUCCUAGCCAUGCACUACUCACCAGACGCCUCAACCGCCUUUUCA
UCAAUCGCCCACAUCACUCGAGACGUAAAUUAUGGCUGAAUCAUCCGCUACCUUCACGCCAAUGG
CGCCUCAAUAUUCUUUAUCUGCCUCUUCCUACACAUCGGGCGAGGCCUAUAUUACGGAUCAUUUC
UCUACUCAGAAACCUGAAACAUCGGCAUUAUCCUCCUGCUUGCAACUAUAGCAACAGCCUUCAUA
GGCUAUGUCCUCCCGUGAGGCCAAAUAUCAUUCUGAGGGGCCACAGUAAUUACAAACUUACU

FIG. 3B continued

AUCCGCCAUCCCAUACAUUGGGACAGACCUAGUUCAAUGAAUCUGAGGA
GGCUACUCAGUAGACAGUCCCACCCUCACACGAUUCUUUACCUUUCACU
UCAUCUUGCCCUUCAUUAUUGCAGCCCUAGCAACACUCCACCUCCUAUU
CUUGCACGAAACGGGAUCAAACAACCCCCUAGGAAUCACCUCCCAUUCC
GAUAAAAUCACCUUCCACCCUUACUACACAAUCAAAGACGCCCUCGGCU
UACUUCUCUUCCUUCUCUCCUUAAUGACAUUAACACUAUUCUCACCAGA
CCUCCUAGGCGACCCAGACAAUUAUACCCUAGCCAACCCCUUAAACACC
CCUCCCCACAUCAAGCCCGAAUGAUAUUUCCUAUUCGCCUACACAAUUC
UCCGAUCCGUCCCUAACAAACUAGGAGGCGUCCUUGCCCUAUUACUAUC
CAUCCUCAUCCUAGCAAUAAUCCCCAUCCUCCAUAUAUCCAAACAACAA CYTB
AGCAUAAUAUUUCGCCCACUAAGCCAAUCACUUUAUUGACUCCUAGCCG
CAGACCUCCUCAUUCUAACCUGAAUCGGAGGACAACCAGUAAGCUACCC
UUUUACCAUCAUUGGACAAGUAGCAUCCGUACUAUACUUCACAACAAUC
CUAAUCCUAAUACCAACUAUCUCCCUAAUUGAAAACAAAAUACUCAAAU CYTB
GGGCCUCGAU

FIG. 3B continued pcRNA-3 pppGGGA*CUGUAGCUCAAUUGGUAGAGCAU*AAGCUU:AUA:CCCAUGGCCAACCUCCUACUCCUCAUU
GUACCCAUUCUAAUCGCAAUGGCAUUCCUAAUGCUUACCGAACGAAAAAUUCUAGGCUAUAUACA
ACUACGCAAAGGCCCCAACGUUGUAGGCCCCUACGGGCUACUACAACCCUUCGCUGACGCCAUAA
AACUCUUCACCAAAGAGCCCCUAAAACCCGCCACAUCUACCAUCACCCUCUACAUCACCGCCCCGA
CCUUAGCUCUCACCAUCGCUCUUCUACUAUGAACCCCCCUCCCCAUACCCAACCCCCUGGUCAACC
UCAACCUAGGCCUCCUAUUUAUUCUAGCCACCUCUAGCCUAGCCGUUUACUCAAUCCUCUGAUCA
GGGUGAGCAUCAAACUCAAACUACGCCCUGAUCGGCGCACUGCGAGCAGUAGCCCAAACAAUCUC
AUAUGAAGUCACCCUAGCCAUCAUUCUACUAUCAACAUUACUAAUAAGUGGCUCCUUUAACCUCUC
CACCCUUAUCACAACACAAGAACACCUCUGAUUACUCCUGCCAUCAUGACCCUUGGCCAUAAUAU
GAUUUAUCUCCACACUAGCAGAGACCAACCGAACCCCCUUCGACCUUGCCGAAGGGGAGUCCGAA
CUAGUCUCAGGCUUCAACAUCGAAUACGCCGCAGGCCCCUUCGCCCUAUUCUUCAUAGCCGAAUA
CACAAACAUUAUUAUAAUAAACACCCUCACCACUACAAUCUUCCUAGGAACAACAUAUGACGCACU
CUCCCCUGAACUCUACACAACAUAUUUUGUCACCAAGACCCUACUUCUAACCUCCCUGUUCUUAUG
AAUUCGAACAGCAUACCCCCGAUUCCGCUACGACCAACUCAUACACCUCCUAUGAAAAAACUUCCU
ACCACUCACCCUAGCAUUACUUAUAUGAUAUGUCUCCAUACCCAUUACAAUCUCCAGCAUUCCCCC
UCAAACC:UAA:GAAAUAUGUCUGAUAAAAGAGUUACUUUGAUAGAGUAAAUAAUAGGAGCUUAAAC
CCCCUUAUUUCUAGGACUAUGAGAAUCGAACCCAUCCCUGAGAAUCCAAAAUUCUCCGUGCCACC
UAUCACACCCCAUCCUAAAGUAAGGUCAGCUAAAUAAGCUAUCGGGCCCAUACCCCGAAAAUGUU
GGUUAUACCCUUCCCGUACUA:AUU:AAUCCCCUGGCCCAACCCGUCAUCUACUCUACCAUCUUUGC
AGGCACACUCAUCACAGCGCUAAGCUCGCACUGAUUUUUUACCUGAGUAGGCCUAGAAAUAAACA
UGCUAGCUUUUAUUCCAGUUCUAACCAAAAAAAUAAACCCUCUAAUAGCUAUCCUCUUCAACAAUA
UACUCUCCGGACAAUGAACCAUAACCAAUACUACCAAUCAAUACUCAUCAUUAAUAAUCAUAAUAG
CUAUAGCAAUAAAACUAGGAAUAGCCCCCUUUCACUUCUGAGUCCCAGAGGUUACCCAAGGCACC
CCUCUGACAUCCGGCCUGCUUCUUCUCACAUGACAAAAACUAGCCCCCAUCUCAAUCAUAUACCAA
AUCUCUCCCUCACUAAACGUAAGCCUUCUCCUCACUCUCUCAAUCUUAUCCAUCAUAGCAGGCAGU
UGAGGUGGAUUAAACCAAACCCAGCUACGCAAAAUCUUAGCAUACUCCUCAAUUACCCACAUAGG
AUGAAUAAUAGCAGUUCUACCGUACAACCCUAACAUAACCAUUCUUAAUUUAACUAUUUAUAUUAU
CCUAACUACUACCGCAUUCCUACUACUCAACUUAAACUCCAGCACCACGACCCUACUACUAUCUCG
CACCUGAAACAAGCUAACAUGACUAACACCCUUAAUUCCAUCCACCCUCCUCUCCCUAGGAGGCC
UGCCCCCGCU

ND1

ND2

COI

FIG. 3C

```
AACCGGCUUUUUGCCCAAAUGGGCCAUUAUCGAAGAAUUCACAAAAAAC
AAUAGCCUCAUCAUCCCCACCAUCAUAGCCACCAUCACCCUCCUUAACCUCUACUUCUACCUACGC
CUAAUCUACUCCACCUCAAUCACACUACUCCCCAUAUCUAACAACGUAAAAAUAAAAUGACAGUUU
GAACAUACAAAACCCACCCCAUUCCUCCCCACACUCAUCGCCCUUACCACGCUACUCCUACCUAUC
UCCCCUUUUAUACUAAUAAUCUUA UAG AAAUUUAGGUUAAAUACAGACCAAGAGCCUUCAAAGCC
CUCAGUAAGUUGCAAUACUUAAUUUCUGUAACAGCUAAGGACUGCAAAACCCCACUCUGCAUCAA
CUGAACGCAAAUCAGCCACUUUAAUUAAGCUAAGCCCUUACUAGACCAAUGGGACUUAAACCCAC
AAACACUUAGUUAACAGCUAAGCACCCUAAUCAACUGGCUUCAAUCUACUUCUCCCGCCGCCGGG
AAAAAAGGCGGGAGAAGCCCCGGCAGGUUUGAAGCUGCUUCUUCGAAUUUGCAAUUCAAUAUGAA
AAUCACCUCGGAGCUGGUAAAAAGAGGCCUAACCCCUGUCUUUAGAUUUACAGUCCAAUGCUUCA
CUCAGCCAUUUUACCUCACCCCCACUG AUG UUCGCCGACCGUUGACUAUUCUCUACAAACCACAA
AGACAUUGGAACACUAUACCUAUUAUUCGGCGCAUGAGCUGGAGUCCUAGGCACAGCUCUAAGCC
UCCUUAUUCGAGCCGAGCUGGGCCAGCCAGGCAACCUUCUAGGUAACGACCACAUCUACAACGUU
AUCGUCACAGCCCAUGCAUUUGUAAUAAUCUUCUUCAUAGUAAUACCCAUCAUAAUCGGAGGCUU
UGGCAACUGACUAGUUCCCCUAAUAAUCGGUGCCCCCGAUAUGGCGUUUCCCCGCAUAAACAACA
UAAGCUUCUGACUCUUACCUCCCUCUCUCCUACUCCUGCUCGCAUCUGCUAUAGUGGAGGCCGGA
GCAGGAACAGGUUGAACAGUCUACCCUCCCUUAGCAGGGAACUACUCCCACCCUGGAGCCUCCGU
AGACCUAACCAUCUUCUCCUUACACCUAGCAGGUGUCUCCUCUAUCUUAGGGGCCAUCAAUUUCA
UCACAACAAUUAUCAAUAUAAAACCCCCUGCCAUAACCCAAUACCAAACGCCCCUCUUCGUCUGAU
CCGUCCUAAUCACAGCAGUCCUACUUCUCCUAUCUCUCCCAGUCCUAGCUGCUGGCAUCACUAUA
CUACUAACAGACCGCAACCUCAACACCACCUUCUUCGACCCCGCCGGAGGAGGAGACCCCAUUCU
AUACCAACACCUAUUCUGAUUUUUCGGUCACCCUGAAGUUUAUAUUCUUAUCCUACCAGGCUUCG
GAAUAAUCUCCCAUAUUGUAACUUACUACUCCGGAAAAAAAGAACCAUUUGGAUACAUAGGUAUG
GUCUGAGCUAUGAUAUCAAUUGGCUUCCUAGGGUUUAUCGUGUGAGCACACCAUAUAUUUACAGU
AGGAAUAGACGUAGACACACGAGCAUAUUUCACCUCCGCUACCAUAAUCAUCGCUAUCCCCACCG
GCGUCAAAGUAUUUAGCUGACUCGCCACACUCCACGGAAGCAAUAUGAAAUGAUCUGCUGCAGUG
CUCUGAGCCCUAGGAUUCAUCUUUCUUUUCACCGUAGGUGGCCUGACUGGCAUUGUAUUAGCAAA
CUCAUCACUAGACAUCGUACUACACGACACGUACUACGUUGUAGCCCACUUCCACUAUGUCCUAU
CAAUAGGAGCUGUAUUUGCCAUCAUAGGAGGCUUCAUUCACUGAUUUCCCCUAUUCUCAGGCUAC
ACCCUAGACCAAACCUACGCCAAAAUCCAUUUCACUAUCAUAUUCAUCGGCGUAAAUCUAACUUUC
UUCCCACAACACUUUCUCGGCCUAUCCGGAAUGCCCCGACGUUACUCGGACUACCCCGAUGCAUA
                                                                CA
```

FIG. 3C continued

CCACAUGAAACAUCCUAUCAUCUGUAGGCUCAUUCAUUUCUCUAACAGC
AGUAAUAUUAAUAAUUUUCAUGAUUUGAGAAGCCUUCGCUUCGAAGCGA
AAAGUCCUAAUAGUAGAAGAACCCUCCAUAAACCUGGAGUGACUAUAUG
GAUGCCCCCCACCCUACCACACAUUCGAAGAACCCGUAUACAUAAAAUC
UAGAGGAUC

FIG. 3C continued

SEQUENCE LISTING

```
<160> NUMBER OF SEQ ID NOS: 20

<210> SEQ ID NO 1
<211> LENGTH: 574
<212> TYPE: PRT
<213> ORGANISM: Leishmania tropica

<400> SEQUENCE: 1

Met Arg Arg Phe Val Ala Gln Tyr Val Ala Pro Ala Met Gly Arg Leu
1               5                   10                  15

Ala Ser Thr Ala Ala Ala Gly Lys Ser Ala Ala Pro Gly Gln Lys Ser
            20                  25                  30

Phe Phe Lys Ala Thr Glu Met Ile Gly Tyr Val His Ser Ile Asp Gly
        35                  40                  45

Thr Ile Ala Thr Leu Ile Pro Ala Pro Gly Asn Pro Gly Val Ala Tyr
    50                  55                  60

Asn Thr Ile Ile Met Ile Gln Val Ser Pro Thr Thr Phe Ala Ala Gly
65                  70                  75                  80

Leu Val Phe Asn Leu Glu Lys Asp Gly Arg Ile Gly Ile Ile Leu Met
                85                  90                  95

Asp Asn Ile Thr Glu Val Gln Ser Gly Gln Lys Val Met Ala Thr Gly
            100                 105                 110

Lys Leu Leu Tyr Ile Pro Val Gly Ala Gly Val Leu Gly Lys Val Val
        115                 120                 125

Asn Pro Leu Gly His Glu Val Pro Val Gly Leu Leu Thr Arg Ser Arg
    130                 135                 140

Ala Leu Leu Glu Ser Glu Gln Thr Leu Gly Lys Val Asp Ala Gly Ala
145                 150                 155                 160

Pro Asn Ile Val Ser Arg Ser Pro Val Asn Tyr Asn Leu Leu Thr Gly
                165                 170                 175

Phe Lys Ala Val Asp Thr Met Ile Pro Ile Gly Arg Gly Gln Arg Glu
```

-continued

```
            180                 185                 190

Leu Ile Val Gly Asp Arg Gln Thr Gly Lys Thr Ser Ile Ala Val Ser
        195                 200                 205

Thr Ile Ile Asn Gln Val Arg Ser Asn Gln Gln Ile Leu Ser Lys Asn
    210                 215                 220

Ala Val Ile Ser Ile Tyr Val Ser Ile Gly Gln Arg Cys Ser Asn Val
225                 230                 235                 240

Ala Arg Ile His Arg Leu Leu Arg Ser Tyr Gly Ala Leu Arg Tyr Thr
                245                 250                 255

Thr Val Met Ala Ala Thr Ala Ala Glu Pro Ala Gly Leu Gln Tyr Leu
            260                 265                 270

Ala Pro Tyr Ser Gly Val Thr Met Gly Glu Tyr Phe Met Asn Arg Gly
        275                 280                 285

Arg His Cys Leu Cys Val Tyr Asp Asp Leu Ser Lys Gln Ala Val Ala
    290                 295                 300

Tyr Arg Gln Ile Ser Leu Leu Leu Arg Arg Pro Pro Gly Arg Glu Ala
305                 310                 315                 320

Tyr Pro Gly Asp Val Phe Tyr Leu His Ser Arg Leu Leu Glu Arg Ala
                325                 330                 335

Ala Met Leu Ser Pro Gly Lys Gly Gly Gly Ser Val Thr Ala Leu Pro
            340                 345                 350

Ile Val Glu Thr Leu Ser Asn Asp Val Thr Ala Tyr Ile Val Thr Asn
        355                 360                 365

Val Ile Ser Ile Thr Asp Gly Gln Ile Tyr Leu Asp Thr Lys Leu Phe
    370                 375                 380

Thr Gly Gly Gln Arg Pro Ala Val Asn Ile Gly Leu Ser Val Ser Arg
385                 390                 395                 400

Val Gly Ser Ser Ala Gln Asn Val Ala Met Lys Ala Val Ala Gly Lys
                405                 410                 415

Leu Lys Gly Ile Leu Ala Glu Tyr Arg Lys Leu Ala Ala Asp Ser Val
            420                 425                 430

Gly Gly Ser Gln Val Gln Thr Val Pro Met Ile Arg Gly Ala Arg Phe
        435                 440                 445

Val Ala Leu Phe Asn Gln Lys Asn Pro Ser Phe Phe Met Asn Ala Leu
    450                 455                 460

Val Ser Leu Tyr Ala Cys Leu Asn Gly Tyr Leu Asp Asp Val Lys Val
465                 470                 475                 480

Asn Tyr Ala Lys Leu Tyr Glu Tyr Leu Leu Val Asn Lys Asp Leu Ser
                485                 490                 495

Val Met Tyr Gly Thr Ala Thr Asn Lys Phe Phe Tyr Met Tyr Val Gln
            500                 505                 510

Gln Leu Asn Tyr Val Ile Arg Phe Phe Thr Leu Asn His Pro Ile Leu
        515                 520                 525

Asn Ala Glu Val Glu Glu Met Leu Lys Gln His Thr His Leu Phe Leu
    530                 535                 540

Gln His Tyr Gln Ser Lys Met Asn Ala Ile Lys Thr Glu Lys Glu Ile
545                 550                 555                 560

Lys Ala Leu Lys Asn Leu Leu Tyr Ser Cys Lys Arg Ala Val
                565                 570


<210> SEQ ID NO 2
<211> LENGTH: 467
<212> TYPE: PRT
<213> ORGANISM: Leishmania tropica
```

-continued

<400> SEQUENCE: 2

```
Met Leu Arg Ala Thr Ser Arg Leu Gly Ile Tyr Glu Tyr Gln Phe Gly
1               5                   10                  15

Gln Pro Ser Leu Lys Asn Ala Phe Ser Thr Arg Ile Thr Pro Ala Ala
            20                  25                  30

Lys Ala Arg Ser Pro Gly Ala Val Gln Ser Thr Lys Leu Thr Asn Gly
        35                  40                  45

Val Arg Val Val Ser His Asp Leu Asp Gly Pro Val Thr Ser Ile Gly
    50                  55                  60

Val Tyr Ala Asp Ala Gly Pro Lys Tyr Asp Pro Ile Ala Thr Pro Gly
65                  70                  75                  80

Leu Ser Tyr Val Met Arg Phe Ala Leu Gln Thr Ser Asn Met Asp Ser
                85                  90                  95

Ser Leu Phe Gln Ile Asp Arg Thr Met Arg Ser Thr Gly Asn Ala Tyr
            100                 105                 110

Gly His Gly Glu Val Cys Lys Arg Tyr Leu Ser Trp Lys Ala Glu Gly
        115                 120                 125

Arg Arg Asp Met Trp Glu Lys Pro Phe Glu Met Leu Ala Thr Gly Val
    130                 135                 140

Val Ala Pro Arg Phe His Glu Ser Asp Ile Glu Arg Phe Arg Asp Thr
145                 150                 155                 160

Met Asp Asn Gln Leu Glu Glu Met Arg Trp Gln Asn Pro Arg Glu Tyr
                165                 170                 175

Ala Ile Asp Gln Leu Glu Thr Val Ala Phe Tyr Lys Glu Pro Leu Gly
            180                 185                 190

Ala Pro Arg Met Val Pro Arg Ile Ala Asn Asp Arg Cys Ser His Lys
        195                 200                 205

Ala Leu Leu Asp His Trp Ala Ala Asn Phe Gln Pro Ser Arg Ile Val
    210                 215                 220

Leu Ala Gly Val Asn Val Pro His Asp Ala Leu Ile Ala Ala Tyr Glu
225                 230                 235                 240

Lys Leu Pro Tyr Lys His Ser Ala Glu Ala Pro His His Ala Arg Ala
                245                 250                 255

Ala Ala Pro Lys Leu Ser His Ser Asn Glu Val Ala Gln Phe Tyr Ala
            260                 265                 270

Gly Arg Gln Asn Val Glu Tyr Glu Ser Arg Ala Ala Val Met Gly Thr
        275                 280                 285

Met Pro Asp Met Gln Ala Glu Val Ile Gly Ala Val Gly Val Pro Thr
    290                 295                 300

His Gly Arg Asp Glu Gly Ala Thr Gln Tyr Ala Thr Ala Leu Val Thr
305                 310                 315                 320

Arg Glu Ile Tyr Glu Glu Ala Met Arg Ser Ala His Gly Ser Arg Ala
                325                 330                 335

Gly Ser Glu His Tyr Gly Ala Gln Val Phe Tyr Arg Pro Tyr Ser Ser
            340                 345                 350

Ala Gly Leu Ile Gly Tyr Thr Val Arg Gly Ala Pro Ala Glu Val Ala
        355                 360                 365

Lys Met Leu Gln Val Ala Ser Ser Ala Phe Pro Ala Ala Val Asp Glu
    370                 375                 380

Ala Ala Val Lys Arg Ala Ala His Cys Ala His Val Arg Leu Leu His
385                 390                 395                 400

Asp Gln Val Glu Met Thr Arg Asp Tyr Cys Asp Phe Leu Ala Thr Ser
```

-continued

```
            405                 410                 415

Pro Asn Ser Val Glu Glu Leu Val Gln Ala Ile Ser Gly Val Thr Lys
        420                 425                 430

Ala Asn Val Glu Glu Ala Met Lys Lys Met Val Ala Gln Lys Pro Ala
    435                 440                 445

Thr Tyr Ala Thr Gly Asp Ser Phe Thr Phe Pro Met Val Ala Ser Leu
    450                 455                 460

Lys His Ala
465


<210> SEQ ID NO 3
<211> LENGTH: 362
<212> TYPE: PRT
<213> ORGANISM: Leishmania tropica

<400> SEQUENCE: 3

Met Ser Leu Lys His Val Ala Ser Phe Gly Ala Val Gly Val Leu Ser
1               5                   10                  15

Val Val Gly Met Leu Gly Gly Arg Arg Trp His Arg Val Glu Leu Arg
            20                  25                  30

Arg Ala Glu Leu Asn Glu Glu Tyr Thr Lys Leu Met Asn Glu Met Arg
        35                  40                  45

Thr Phe Asn Glu Lys Arg Leu Thr Arg Asp Glu Arg Leu Ala Ala Lys
    50                  55                  60

Glu Ala Glu Ala Lys Val Thr Ala Glu Thr Val Asp Ile Leu Trp Ser
65                  70                  75                  80

Asp Arg Leu Ala Arg Tyr Ala Gln Val Asn Lys Asp Leu His Ala Tyr
                85                  90                  95

Leu Ala Ala Leu Pro Glu Ala Ile Gly Val Leu Lys Gly Leu Ser Asn
            100                 105                 110

His Tyr Arg Tyr Met Ser Glu Glu Met Pro Lys Phe Thr Gly Phe Asp
        115                 120                 125

Ile Ala Cys Ser Lys Met His Asn Leu Ala Leu Met Leu Glu His Gly
    130                 135                 140

Lys Ala Val Gly Ile Glu Arg Val Ala Ala Thr Val Gln Ala Met Phe
145                 150                 155                 160

Val Ala Glu Pro Leu Val Gln Ala Val Cys Thr Ser Ile Leu Ala Ala
                165                 170                 175

Pro Ala Pro Pro His Pro Ser Ser Ile Ala Ala Ala Ser Ala Ala Phe
            180                 185                 190

Thr Phe Cys Met Glu Glu Leu Asp Arg Ala Val Gly Thr Val Ala Met
        195                 200                 205

Arg Tyr Ala Ala Ala Leu Glu Glu Pro Pro Asn Ala Thr Pro Gly Ile
    210                 215                 220

Leu Ser Asp Ser Val Arg Lys Leu Val Ser Met Met Arg Thr Asp Thr
225                 230                 235                 240

Leu Cys Lys Gly Gln Arg Gln Leu Ala Glu Arg Arg Arg Asp Leu Glu
                245                 250                 255

Arg Thr Leu Arg Arg Ala Gln Arg Gln Leu His Thr Glu Glu Asp Ile
            260                 265                 270

Arg Ala Ala Leu Asp Tyr Thr Arg Glu Leu Asp Gln His Leu Gln Ala
        275                 280                 285

Ala Ala Pro Arg Arg Thr Asp Leu Leu Leu Ser Ser Pro Ser Arg Lys
    290                 295                 300
```

```
Asp Asn Phe Leu Ala Ala Val Arg Ser Asp Ser Glu Val Lys Lys Ala
305                 310                 315                 320

Ile Gln Gln Ile Asp Leu Trp Arg Asp Ser Ala Thr Thr Phe Leu Val
                325                 330                 335

His Arg Gln Ala Glu Asp Ala Leu Gln Ser Tyr Tyr Phe Leu Leu Ala
            340                 345                 350

Glu Thr Leu Thr Ala Val Asn Glu Leu Lys
        355                 360


<210> SEQ ID NO 4
<211> LENGTH: 342
<212> TYPE: PRT
<213> ORGANISM: Leishmania tropica

<400> SEQUENCE: 4

Met Leu Thr Arg Arg Ala Val Ser Ser Ala Val Gly Ala Ala Met Val
1               5                   10                  15

Thr Ser Ser Ser Val Ser Met Gln Arg Arg Tyr Asp His Asp Arg Trp
            20                  25                  30

Tyr Gly His Ala Leu Glu Leu Asp Thr His Asn Tyr Lys Phe Asn Gly
        35                  40                  45

Glu Pro Pro Ser Trp Met Lys Thr Arg Ala Lys Thr Glu Glu Thr Ser
    50                  55                  60

Phe Ala Lys Ser Val Leu Pro His Ile Asp Phe Ala Ser Ser Tyr Glu
65                  70                  75                  80

Cys Leu Leu Phe Asp Ala Asp Arg Leu Asn Thr Asn Leu Asn Arg Lys
                85                  90                  95

Glu Phe Gly Asn Glu Ile Lys Tyr Arg Leu Glu Lys Gln Ala Asn Thr
            100                 105                 110

Val Ala Arg Ala Gln Gln Leu Leu Arg Asp Lys Lys Ala Gly Thr Gly
        115                 120                 125

Pro Asp Ala Glu Lys Val Glu Asn Thr Leu Ile Ala Arg Ile Phe Asp
    130                 135                 140

Glu Glu His Val Gln Ala Glu Met Lys Tyr Val Lys Cys Ile Arg Ala
145                 150                 155                 160

Asn Glu Leu Ala Glu Asp Asn Arg Leu Asp Ile Leu Pro Gly Gly Ser
                165                 170                 175

Pro Asn Ser Leu Arg Glu Lys Thr Arg Trp Asn Leu Asn Thr Glu Leu
            180                 185                 190

His Pro Ala Asp Arg Ala Glu Ile Gly Ala Arg Leu Thr Ala Trp Leu
        195                 200                 205

Pro Glu Lys Tyr His Ile Val Tyr Phe Asp Asp Phe Gln Thr Val Ala
    210                 215                 220

Ala Asn Asp Ala Thr Ala Arg Lys Glu Met Leu Glu Ile Val Glu Ser
225                 230                 235                 240

Val Gln Lys Glu Tyr Thr Ala Glu Ala Lys Glu Gly Gly Tyr Glu Ser
                245                 250                 255

Asp Leu Lys Glu Ala Val Ala Glu Leu Met Asp Asp Val Asp Pro Thr
            260                 265                 270

Arg Thr Ile Thr Met Glu Ala Ile Lys Ser Cys Lys Asp Leu Gln Gln
        275                 280                 285

Leu Glu Asp Trp Ser Arg Gln Val His Glu Tyr Asn Gly Asp Asp Arg
    290                 295                 300

Ile Ile Ala Ile Tyr Ala Arg Ala Ala Glu Ile Thr Lys Asn Val Glu
305                 310                 315                 320
```

```
His Gln Ala Leu Val Arg Gln Met Arg Glu Trp Arg Lys Leu Ala Thr
                325                 330                 335

Lys Asn Glu Ser Lys Leu
            340


<210> SEQ ID NO 5
<211> LENGTH: 296
<212> TYPE: PRT
<213> ORGANISM: Leishmania tropica

<400> SEQUENCE: 5

Met Phe Arg Arg Ser Phe Ile Ser Ala Phe Gln Ala Thr Arg Pro Ala
1               5                   10                  15

Arg Val Ser Leu Val Phe Lys Gln Leu Glu Gly Asn Met Pro Leu Thr
            20                  25                  30

Lys Lys Asp Lys Pro Val Asp Ser Trp Ser Asp Glu Phe Met Lys Pro
        35                  40                  45

Pro Gln Ser Ala Glu Met Thr Lys Lys Tyr Gly Arg Tyr Ala Lys Tyr
    50                  55                  60

Ser Asp Pro Ala Leu Cys Asp Val Asp Thr Ser Asp Glu Val Val Leu
65                  70                  75                  80

Asn Thr Tyr Pro Glu Gly Ala Pro Gln Gly Arg Ile Glu Ala Thr Ala
                85                  90                  95

Gly Val Ala Leu Lys Asp Tyr Asp Ala Ser Met Trp Asp Glu Glu Phe
            100                 105                 110

Phe Arg Lys His Ile Leu Lys Pro Lys Leu Ala Asp Asp Met Glu Asp
        115                 120                 125

Arg Ala Arg Val Thr Asp Tyr Ala Leu Asn Ser Ala Met Leu Gly Phe
    130                 135                 140

Val Ile Leu Met Ala Arg Tyr Ala Val Leu Pro Leu Trp Tyr Val Gly
145                 150                 155                 160

Gln Pro Ala Met Ser Met Val Gly Gln Met Asn Ile Glu Ala Glu Val
                165                 170                 175

Gly Glu Leu Asp Glu Arg Gln Cys Thr Thr Val Val Trp Gly Lys Pro
            180                 185                 190

Val Phe Val Tyr Arg Arg Ser Ala Arg Gln Met Lys Glu Val Met Glu
        195                 200                 205

Thr Pro Leu Ser Ala Leu Lys Asp Pro Glu Thr Asp Glu Ala Arg Phe
    210                 215                 220

Pro Asp His Arg Asp Lys Ala Val Val Ile Ala Ile Cys Thr His Leu
225                 230                 235                 240

Gly Cys Val Pro Ile Pro Asn Glu Gly Leu Phe Asn Gly Phe Phe Cys
                245                 250                 255

Pro Cys His Gly Ser His Tyr Asp Pro Ser Gly Arg Ile Arg Gln Gly
            260                 265                 270

Pro Ala Pro Leu Asn Leu Glu Val Pro Pro Tyr Arg Trp Ile Asp Asp
        275                 280                 285

His Thr Ile Tyr Met Gly Lys Leu
    290                 295


<210> SEQ ID NO 6
<211> LENGTH: 202
<212> TYPE: PRT
<213> ORGANISM: Leishmania tropica

<400> SEQUENCE: 6
```

```
Met Met Lys Pro Thr Ser Pro Asn Phe Met Ala Gln Gly Ile Trp Ala
1               5                   10                  15

Gly Phe Arg Tyr Tyr Ile Gly His Phe Phe Tyr Pro Asn Met Tyr Arg
            20                  25                  30

Glu Phe Leu Ser Val Gln Asn Ala His Lys Val Glu Arg Ala Leu Arg
        35                  40                  45

Leu Gln Lys Ala Ile Lys Ala Asn Lys Ile Asp Tyr Arg Ala Leu Leu
    50                  55                  60

Ala Leu Pro Val Thr Asp His Ala His Pro Tyr Lys Met Glu Tyr Pro
65                  70                  75                  80

Trp Glu Lys Val Met Gln Ser Asp Ala Arg Asp Leu Gly Phe Tyr Gly
                85                  90                  95

Lys Trp Tyr Ala Ser Lys Met Met Cys Phe Tyr Glu Gly Leu Gln Phe
            100                 105                 110

His Lys Trp Gly Cys Leu Gln Asp Asp Leu Ile Asn Ala His Gly Trp
        115                 120                 125

Trp Asn Arg Ala Ala Arg Thr Arg Ala Pro Lys Asp Lys Val Val His
    130                 135                 140

Gly Asp Arg Arg Val Met Arg Ala Arg Val Leu Lys Asp Lys Tyr Ile
145                 150                 155                 160

Tyr Glu Pro Lys Asp Arg Trp Val His Pro Val Asp Asn Val Ala Tyr
                165                 170                 175

Phe Gly Pro Tyr Val Met Met Val Ala Asp Glu Trp Glu Glu Lys Trp
            180                 185                 190

Gly Phe Phe Ala Gly Gln Glu Val Glu Tyr
        195                 200


<210> SEQ ID NO 7
<211> LENGTH: 191
<212> TYPE: PRT
<213> ORGANISM: Leishmania tropica

<400> SEQUENCE: 7

Met Thr Met Asn Phe Gly Asn Met Thr Leu Gly Gly Ala Met Ala Thr
1               5                   10                  15

Phe Gly Gly Gln Ser Asn Pro Met Cys Asn Tyr Thr Ser Pro Leu Ala
            20                  25                  30

Lys Lys Phe Val Tyr Lys Glu Val Gly Lys Val Tyr Tyr Pro Leu Arg
        35                  40                  45

Arg His Val Phe Arg Thr Lys Val Arg Thr Ala Ala Glu Ile Arg Phe
    50                  55                  60

Asn Glu Ile Val Lys Arg Tyr Met Lys Glu Lys Met Thr Phe Lys Arg
65                  70                  75                  80

Gly Cys Tyr Ala Ala Thr Ile Thr Asn Thr Val Glu Leu Asp His Met
                85                  90                  95

Gly Ser Ile Ile Pro Lys Asp Glu Tyr Glu Val Lys Arg Leu Thr Ser
            100                 105                 110

Tyr Met Thr Ser Lys Lys Met Ser Asn Asp Tyr Lys Lys His Met Gln
        115                 120                 125

Glu Leu Trp Thr Arg Val Leu Phe Val Cys Glu Ser Thr Asn Leu Val
    130                 135                 140

Gly Val Thr Glu Asn Ala Met His Gln Asn Ser Arg Pro Gly Thr Asp
145                 150                 155                 160

Glu Glu Phe Met Ser Leu Ile Trp Tyr Ser Ser Phe Val Thr Thr Leu
```

```
                165                 170                 175

Met Ala Phe Val Val Thr Leu Cys Ile Trp Trp Tyr Arg Tyr Gly
            180                 185                 190


<210> SEQ ID NO 8
<211> LENGTH: 157
<212> TYPE: PRT
<213> ORGANISM: Leishmania tropica

<400> SEQUENCE: 8

Met Pro His Glu Asp His Lys Lys Tyr Arg Val Gln Arg Glu Asp Leu
1               5                   10                  15

Pro Ala Met Pro His Phe Ser Asp Phe Asn Asp Pro Arg Phe Cys Gly
            20                  25                  30

Thr Thr Asn Lys Gln Lys Asn Gly Ile Leu Ala Tyr Tyr Gln Trp Leu
        35                  40                  45

His Cys Ile Gly Asn Trp Gly Glu Glu His Ser Met Cys Lys Lys Met
    50                  55                  60

Arg Trp Tyr Val Glu Arg Met Met His Glu Thr Trp Leu Glu Lys Trp
65                  70                  75                  80

Glu Glu Lys Arg Ala Leu Gly His Phe Asp His Thr Val Leu Tyr Gly
                85                  90                  95

Val Lys Pro Trp Lys Glu Phe Glu Pro Leu Tyr Gln Pro Val Lys Lys
            100                 105                 110

Asn Arg Lys Gly Ala Tyr Glu Tyr Trp Leu Asp Arg Asp Phe Glu Pro
        115                 120                 125

Leu Tyr Asp Val Asp Ala Ala Asp Trp Arg Glu Arg Ala Pro Ile Leu
    130                 135                 140

His Asp Met Phe Val Leu Gly Lys Lys Pro Val Ser Glu
145                 150                 155


<210> SEQ ID NO 9
<211> LENGTH: 4128
<212> TYPE: RNA
<213> ORGANISM: Leishmania tropica

<400> SEQUENCE: 9

gggacuguag cucaauuggu agagcaugga uccauguucg ccgaccguug acuauucucu      60

acaaaccaca aagacauugg aacacuauac cuauuauucg gcgcaugagc uggaguccua     120

ggcacagcuc uaagccuccu uauucgagcc gagcugggcc agccaggcaa ccuucuaggu     180

aacgaccaca ucuacaacgu uaucgucaca gcccaugcau uuguaauaau cuucuucaua     240

guaauaccca ucauaaucgg aggcuuuggc aacugacuag uuccccuaau aaucggugcc     300

cccgauaugg cguuuccccg cauaaacaac auaagcuucu gacucuuacc ucccucucuc     360

cuacuccugc ucgcaucugc uauaguggag gccggagcag gaacagguug aacagucuac     420

ccucccuuag cagggaacua cucccacccu ggagccuccg uagaccuaac caucuucucc     480

uuacaccuag caggugucuc cucuaucuua ggggccauca auuucaucac aacaauuauc     540

aauauaaaac ccccugccau aacccaauac caaacgcccc ucuucgucug auccguccua     600

aucacagcag uccuacuucu ccuaucucuc ccaguccuag cugcuggcau cacuauacua     660

cuaacagacc gcaaccucaa caccaccuuc uucgaccccg ccggaggagg agaccccauu     720

cuauaccaac accuauucug auuuuucggu cacccugaag uuuauauucu uauccuacca     780

ggcuucggaa uaaucuccca uauuguaacu uacuacuccg gaaaaaaaga accauuugga     840
```

-continued

```
uacauaggua uggucugagc uaugauauca auuggcuucc uaggguuuau cgugugagca    900
caccauauau uuacaguagg aauagacgua gacacacgag cauauuucac cuccgcuacc    960
auaaucaucg cuauccccac cggcgucaaa guauuuagcu gacucgccac acuccacgga   1020
agcaauauga aaugaucugc ugcagugcuc ugagcccuag gauucaucuu ucuuuucacc   1080
guagguggcc ugacuggcau uguauuagca aacucaucac uagacaucgu acuacacgac   1140
acguacuacg uuguagccca cuuccacuau guccuaucaa uaggagcugu auuugccauc   1200
auaggaggcu ucauucacug auuuccccua uucucaggcu acacccuaga ccaaaccuac   1260
gccaaaaucc auuucacuau cauauucauc ggcguaaauc uaacuuucuu cccacaacac   1320
uuucucggcc uauccggaau gccccgacgu uacucggacu accccgaugc auacaccaca   1380
ugaaacaucc uaucaucugu aggcucauuc auuucucuaa cagcaguaau auuaauaauu   1440
uucaugauuu gagaagccuu cgcuucgaag cgaaaagucc uaauaguaga agaacccucc   1500
auaaaccugg agugacuaua uggaugcccc ccacccuacc acacauucga agaacccgua   1560
uacauaaaau cuagacaaaa aaggaaggaa ucgaaccccc caaagcuggu uucaagccaa   1620
ccccauggcc uccaugacuu uuucaaaaag guauuagaaa aaccauuuca uaacuuuguc   1680
aaaguuaaau uauaggcuaa auccuauaua ucuuaauggc acaugcagcg caaguagguc   1740
uacaagacgc uacuuccccu aucauagaag agcuuaucac cuuucaugau cacgcccuca   1800
uaaucauuuu ccuuaucugc uuccuagucc uguaugcccu uuuccuaaca cucacaacaa   1860
aacuaacuaa uacuaacauc ucagacgcuc aggaaauaga aaccgucuga acuauccugc   1920
ccgccaucau ccuaguccuc aucgcccucc caucccuacg cauccuuuac auaacagacg   1980
aggucaacga ucccucccuu accaucaaau caauuggcca ccaaugguac ugaaccuacg   2040
aguacaccga cuacggcgga cuaaucuuca acuccuacau acuuccccca uuauuccuag   2100
aaccaggcga ccugcgacuc cuugacguug acaaucgagu aguacucccg auugaagccc   2160
ccauucguau aauaauuaca ucacaagacg ucuugcacuc augagcuguc cccacauuag   2220
gcuuaaaaac agaugcaauu cccggacguc uaaaccaaac cacuuucacc gcuacacgac   2280
cggggguaua cuacggucaa ugcucugaaa ucuguggagc aaaccacagu uucaugccca   2340
ucguccuaga auuaauuccc cuaaaaaucu uugaaauagg gcccguauuu acccuauagc   2400
acccccucua cccccucuag agcccacugu aaagcuaacu uagcauuaac cuuuuaaguu   2460
aaagauuaag agaaccaaca ccucuuuaca gugaaaugcc ccaacuaaau acuaccguau   2520
ggcccaccau aauuaccccc auacuccuua cacuauuccu caucacccaa cuaaaaauau   2580
uaaacacaaa cuaccaccua ccucccucac caaagcccau aaaaauaaaa aauuauaaca   2640
aacccugaga accaaaauga acgaaaaucu guucgcuuca uucauugccc ccacaauccu   2700
aggccuaccc gccgcaguac ugaucauucu auuuccccccu cuauugaucc ccaccuccaa   2760
auaucucauc aacaaccgac uaaucaccac ccaacaauga cuaaucaaac uaaccucaaa   2820
acaaaugaua accauacaca acacuaaagg acgaaccuga ucucuuauac uaguauccuu   2880
aaucauuuuu auugccacaa cuaaccuccu cggacuccug ccucacucau uuacaccaac   2940
cacccaacua ucuauaaacc uagccauggc cauccccuua ugagcgggca cagugauuau   3000
aggcuuucgc ucuaagauua aaaaugcccu agcccacuuc uuaccacaag gcacaccuac   3060
accccuuauc cccauacuag uuauuaucga aaccaucagc cuacucauuc aaccaauagc   3120
ccuggccgua cgccuaaccg cuaacauuac ugcaggccac cuacucaugc accuaauugg   3180
aagcgccacc cuagcaauau caaccauuaa ccuucccucu acacuuauca ucuucacaau   3240
```

-continued ucuaauucua cugacuaucc uagaaaucgc ugucgccuua auccaagccu acguuuucac 3300
acuucuagua agccucuacc ugcacgacaa cacauaauga cccaccaauc acaugccuau 3360
cauauaguaa aacccagccc augaccccua acaggggccc ucucagcccu ccuaaugacc 3420
uccggccuag ccaugugauu ucacuuccac uccauaacgc uccucauacu aggccuacua 3480
accaacacac uaaccauaua ccaaugaugg cgcgauguaa cacgagaaag cacauaccaa 3540
ggccaccaca caccaccugu ccaaaaaggc cuucgauacg ggauaauccu auuuauuacc 3600
ucagaaguuu uuuucuucgc aggauuuuuc ugagccuuuu accacuccag ccuagccccu 3660
accccccaau uaggagggca cuggccccca acaggcauca ccccgcuaaa uccccuagaa 3720
gucccacucc uaaacacauc cguauuacuc gcaucaggag uaucaaucac cugagcucac 3780
cauagucuaa uagaaaacaa ccgaaaccaa auaauucaag cacugcuuau uacaauuuua 3840
cugggucucu auuuuacccu ccuacaagcc ucagaguacu ucgagucucc cuucaccauu 3900
uccgacggca ucuacggcuc aacauuuuuu guagccacag gcuuccacgg acuucacguc 3960
auuauuggcu caacuuuccu cacuaucugc uucauccgcc aacuaauauu ucacuuuaca 4020
uccaaacauc acuuuggcuu cgaagccgcc gccugauacu ggcauuuugu agaugugguu 4080
ugacuauuuc uguaugucuc caucuauuga ugagggucuu ggauccgc 4128

<210> SEQ ID NO 10
<211> LENGTH: 6718
<212> TYPE: RNA
<213> ORGANISM: Leishmania tropica

<400> SEQUENCE: 10
gggacuguag cucaauuggu agagcaugga uccaugaccc accaaucaca ugccuaucau 60
auaguaaaac ccagcccaug accccuaaca ggggcccucu cagcccuccu aaugaccucc 120
ggccuagcca ugugauuuca cuuccacucc auaacgcucc ucauacuagg ccuacuaacc 180
aacacacuaa ccauauacca augauggcgc gauguaacac gagaaagcac auaccaaggc 240
caccacacac caccugucca aaaaggccuu cgauacggga uaauccuauu uauuaccuca 300
gaaguuuuuu ucuucgcagg auuuuucuga gccuuuuacc acuccagccu agccccuacc 360
ccccaauuag gagggcacug gcccccaaca ggcaucaccc cgcuaaaucc ccuagaaguc 420
ccacuccuaa acacauccgu auuacucgca ucaggaguau caaucaccug agcucaccau 480
agucuaauag aaaacaaccg aaaccaaaua auucaagcac ugcuuauuac aauuuuacug 540
ggucucuauu uuacccuccu acaagccuca gaguacuucg agucucccuu caccauuucc 600
gacggcaucu acggcucaac auuuuuugua gccacaggcu uccacggacu ucacgucauu 660
auuggcucaa cuuuccucac uaucugcuuc auccgccaac uaauauuuca cuuuacaucc 720
aaacaucacu uuggcuucga agccgccgcc ugauacuggc auuuuguaga ugugguuuga 780
cuauuucugu auguccccau cuauugauga gggucuuacu cuuuuaguau aaauaguacc 840
guuaacuucc aauuaacuag uuuugacaac auucaaaaaa gaguaauaaa cuucgccuua 900
auuuuaauaa ucaacacccu ccuagccuua cuacuaauaa uuauuacauu uugacuacca 960
caacucaacg gcuacauaga aaaauccacc ccuuacgagu gcggcuucga cccuauaucc 1020
cccgcccgcg ucccuuucuc cauaaaauuc uucuuaguag cuauuaccuu cuuauuauuu 1080
gaucuagaaa uugcccuccu uuuaccccua ccaugagccc uacaaacaac uaaccugcca 1140
cuaauaguua ugucaucccu cuuauuaauc aucauccuag cccuaagucu ggccuaugag 1200

-continued

```
ugacuacaaa aaggauuaga cugaaccgaa uugguauaua guuuaaacaa aacgaaugau   1260
uucgacucau uaaauuauga uaaucauauu uaccaaaugc cccucauuua cauaaauauu   1320
auacuagcau uuaccaucuc acuucuagga auacuaguau aucgcucaca ccucauaucc   1380
ucccuacuau gccuagaagg aauaauacua ucgcuguuca uuauagcuac ucucauaacc   1440
cucaacaccc acucccucuu agccaauauu gugccuauug ccauacuagu cuuugccgcc   1500
ugcgaagcag cggugggccu agcccuacua gucucaaucu ccaacacaua uggccuagac   1560
uacguacaua accuaaaccu acuccaaugc uaaaacuaau cgucccaaca auuauauuac   1620
uaccacugac augacuuucc aaaaaacaca uaauuugaau caacacaacc acccacagcc   1680
uaauuauuag caucaucccu cuacuauuuu uuaaccaaau caacaacaac cuauuuagcu   1740
guuccccaac cuuuuccucc gacccccuaa caaccccccu ccuaauacua acuaccugac   1800
uccuaccccu cacaaucaug gcaagccaac gccacuuauc cagugaacca cuaucacgaa   1860
aaaaacucua ccucucuaua cuaaucuccc uacaaaucuc cuuaauuaua acauucacag   1920
ccacagaacu aaucauauuu uauaucuucu ucgaaaccac acuuaucccc accuuggcua   1980
ucaucacccg augaggcaac cagccagaac gccugaacgc aggcacauac uuccuauucu   2040
acacccuagu aggcucccuu ccccuacuca ucgcacuaau uuacacucac aacacccuag   2100
gcucacuaaa cauucuacua cucacucuca cugcccaaga acuaucaaac uccugagcca   2160
acaacuuaau augacuagcu uacacaauag cuuuuauagu aaagauaccu cuuuacggac   2220
uccacuuaug acucccuaaa gcccaugucg aagcccccau cgcugggguca auaguacuug   2280
ccgcaguacu cuuaaaacua ggcggcuaug guauaaauacg ccucacacuc auucucaacc   2340
cccugacaaa acacauagcc uaccccuucc uuguacuauc ccuaugaggc auaauuauaa   2400
caagcuccau cugccuacga caaacagacc uaaaaucgcu cauugcauac ucuucaauca   2460
gccacauagc ccucguagua acagccauuc ucauccaaac ccccugaagc uucaccggcg   2520
cagucauucu cauaaucgcc cacgggcuua cauccucauu acuauucugc cuagcaaacu   2580
caaacuacga acgcacucac agucgcauca uaauccucuc ucaaggacuu caaacucuac   2640
ucccacuaau agcuuuuuga ugacuucuag caagccucgc uaaccucgcc uuacccccca   2700
cuauuaaccu acugggagaa cucucugugc uaguaaccac guucuccuga ucaaauauca   2760
cucuccuacu uacaggacuc aacauacuag ucacagcccu auacucccuc uacauauuua   2820
ccacaacaca auggggcuca cucacccacc acauuaacaa cauaaaaccc ucauucacac   2880
gagaaaacac ccucauguuc auacaccuau cccccauucu ccuccuaucc cucaaccccg   2940
acaucauuac cggguuuucc ucuuguaaau auaguuuaac caaaacauca gauugugaau   3000
cugacaacag aggcuuacga ccccuuauuu accgagaaag cucacaagaa cugcuaacuc   3060
augcccccau gucuaacaac auggcuuucu caacuuuuaa aggauaacag cuauccauug   3120
gucuuaggcc ccaaaaauuu uggugcaacu ccaaauaaaa guaauaacca ugcacacuac   3180
uauaaccacc cuaacccuga cuucccuaau ucccccauc cuuaccaccc ucguuaaccc   3240
uaacaaaaaa aacucauacc cccauuaugu aaaauccauu gucgcaucca ccuuuauuau   3300
cagucucuuc cccacaacaa uauucaugug ccuagaccaa gaaguuauua ucucgaacug   3360
acacugagcc acaacccaaa caacccagcu cucccuaagc uucaaacuag acuacuucuc   3420
cauaauauuc aucccuguag cauuguucgu uacaugg ucc aucauagaau ucucacugug   3480
auauauaaac ucagacccaa acauuaauca guucuucaaa uaucuacuca ucuuccuaau   3540
uaccauacua aucuuaguua ccgcuaacaa ccuauuccaa cuguucaucg gcugagaggg   3600
```

-continued cguaggaauu auauccuucu ugcucaucag uugaugauac gcccgagcag augccaacac 3660
agcagccauu caagcaaucc uauacaaccg uaucggcgau aucgguuuca uccucgccuu 3720
agcaugauuu auccuacacu ccaacucaug agacccacaa caaauagccc uucuaaacgc 3780
uaauccaagc cucaccccac uacuaggccu ccuccuagca gcagcaggca aaucagccca 3840
auuaggucuc caccccugac uccccucagc cauagaaggc cccaccccag ucucagcccu 3900
acuccacuca agcacuauag uuguagcagg aaucuucuua cucauccgcu uccacccccu 3960
agcagaaaau agcccacuaa uccaaacucu aacacuaugc uuaggcgcua ucaccacucu 4020
guucgcagca gucugcgccc uuacacaaaa ugacaucaaa aaaaucguag ccuucuccac 4080
uucaagucaa cuaggacuca uaauaguuac aaucggcauc aaccaaccac accuagcauu 4140
ccugcacauc uguacccacg ccuucuucaa agccauacua uuuaugugcu ccggguccau 4200
cauccacaac cuuaacaaug aacaagauau ucgaaaaaua ggaggacuac ucaaaaccau 4260
accucucacu ucaaccuccc ucaccauugg cagccuagca uuagcaggaa uaccuuuccu 4320
cacagguuuc uacuccaaag accacaucau cgaaaccgca aacauaucau acacaaacgc 4380
cugagcccua ucuauuacuc ucaucgcuac cucccugaca agcgccuaua gcacucgaau 4440
aauucuucuc acccuaacag gucaaccucg cuuccccacc cuuacuaaca uuaacgaaaa 4500
uaaccccacc cuacuaaacc ccauuaaacg ccuggcagcc ggaagccuau ucgcaggauu 4560
ucucauuacu aacaacauuu cccccgcauc ccccuuccaa acaacaaucc cccucuaccu 4620
aaaacucaca gcccucgcug ucacuuuccu aggacuucua acagcccuag accucaacua 4680
ccuaaccaac aaacuuaaaa uaaaaucccc acuaugcaca uuuuauuucu ccaacauacu 4740
cggauucuac ccuagcauca cacaccgcac aauccccuau cuaggccuuc uuacgagcca 4800
aaaccugccc cuacuccucc uagaccuaac cugacuagaa aagcuauuac cuaaaacaau 4860
uucacagcac caaaucucca ccuccaucau caccucaacc caaaaaggca uaauuaaacu 4920
uuacuucccuc ucuuucuucu ucccacucau ccuaacccua cuccuaauca cauaaccuau 4980
ucccccgagc aaucucaauu acaauauaua caccaacaaa caauguucaa ccaguaacua 5040
cuacuaauca acgcccauaa ucauacaaag cccccgcacc aauaggaucc ucccgaauca 5100
acccugaccc cucuccuuca uaaauuauuc agcuuccuac acuauuaaag uuuaccacaa 5160
ccaccacccc aucauacucu uucacccaca gcaccaaucc uaccuccauc gcuaacccca 5220
cuaaaacacu caccaagacc ucaaccccug acccccaugc cucaggauac uccucaauag 5280
ccaucgcugu aguauaucca aagacaacca ucauuccccc uaaauaaauu aaaaaaacua 5340
uuaaacccau auaaccuccc ccaaaauuca gaauaauaac acacccgacc acaccgcuaa 5400
caaucaauac uaaaccccca uaaauaggag aaggcuuaga agaaaacccc acaaacccca 5460
uuacuaaacc cacacucaac agaaacaaag cauacaucau uauucucgca cggacuacaa 5520
ccacgaccaa ugauaugaaa aaccaucguu guauuucaac uacaagaaca ccaaugaccc 5580
caauacgcaa aacuaacccc cuaauaaaau uaauuaacca cucauucauc gaccuccccca 5640
ccccauccaa caucuccgca ugaugaaacu ucggcucacu ccuuggcgcc ugccugaucc 5700
uccaaaucac cacaggacua uuccuagcca ugcacuacuc accagacgcc ucaaccgccu 5760
uuucaucaau cgcccacauc acucgagacg uaaauuaugg cugaaucauc cgcuaccuuc 5820
acgccaaugg cgccucaaua uucuuuaucu gccucuuccu acacaucggg cgaggccuau 5880
auuacggauc auuucucuac ucagaaaccu gaaacaucgg cauuauccuc cugcuugcaa 5940

-continued

```
cuauagcaac agccuucaua ggcuaugucc ucccgugagg ccaaauauca uucugagggg   6000

ccacaguaau uacaaacuua cuauccgcca ucccauacau ugggacagac cuaguucaau   6060

gaaucugagg aggcuacuca guagacaguc ccacccucac acgauucuuu accuuucacu   6120

ucaucuugcc cuucauuauu gcagcccuag caacacucca ccuccuauuc uugcacgaaa   6180

cgggaucaaa caaccccua ggaaucaccu cccauuccga uaaaaucacc uuccacccuu   6240

acuacacaau caaagacgcc cucggcuuac uucucuuccu ucucuccuua augacauuaa   6300

cacuauucuc accagaccuc cuaggcgacc cagacaauua uacccuagcc aaccccuuaa   6360

acaccccucc ccacaucaag cccgaaugau auuuccuauu cgccuacaca auucuccgau   6420

ccgucccuaa caaacuagga ggcguccuug cccuauuacu auccauccuc auccuagcaa   6480

uaaucccau ccuccauaua uccaaacaac aaagcauaau auuucgccca cuaagccaau   6540

cacuuuauug acuccuagcc gcagaccucc ucauucuaac cugaaucgga ggacaaccag   6600

uaagcuaccc uuuuaccauc auuggacaag uagcauccgu acuauacuuc acaacaaucc   6660

uaauccuaau accaacuauc ucccuaauug aaaacaaaau acucaaaugg gccucgau     6718
```

<210> SEQ ID NO 11
<211> LENGTH: 4117
<212> TYPE: RNA
<213> ORGANISM: Leishmania tropica

<400> SEQUENCE: 11

```
gggacuguag cucaauuggu agagcauaag cuuauaccca uggccaaccu ccuacuccuc     60

auuguaccca uucuaaucgc aauggcauuc cuaaugcuua ccgaacgaaa aauucuaggc    120

uauauacaac uacgcaaagg ccccaacguu guaggccccu acgggcuacu acaacccuuc    180

gcugacgcca uaaaacucuu caccaaagag ccccuaaaac ccgccacauc uaccaucacc    240

cucuacauca ccgccccgac cuuagcucuc accaucgcuc uucuacuaug aacccccuc    300

cccauaccca accccuggu caaccucaac cuaggccucc uauuuauucu agccaccucu    360

agccuagccg uuuacucaau ccucugauca gggugagcau caaacucaaa cuacgcccug    420

aucggcgcac ugcgagcagu agcccaaaca aucucauaug aagucacccu agccaucauu    480

cuacuaucaa cauuacuaau aaguggcucc uuuaaccucu ccacccuuau cacaacacaa    540

gaacaccucu gauuacuccu gccaucauga cccuuggcca uaauaugauu uaucuccaca    600

cuagcagaga ccaaccgaac cccuucgac cuugccgaag gggaguccga acuagucuca    660

ggcuucaaca ucgaauacgc cgcaggcccc uucgcccuau ucuucauagc cgaauacaca    720

aacauuauua uaauaaacac ccucaccacu acaaucuucc uaggaacaac auaugacgca    780

cucuccccug aacucuacac aacauauuuu gucaccaaga cccuacuucu aaccucccug    840

uucuuaugaa uucgaacagc auaccccga uuccgcuacg accaacucau acaccuccua    900

ugaaaaaacu uccuaccacu cacccuagca uuacuuauau gauaugucuc cauacccauu    960

acaaucucca gcauuccccc ucaaaccuaa gaaauauguc ugauaaaaga guuacuuuga   1020

uagaguaaau aauaggagcu uaaaccccu uauuucuagg acuaugagaa ucgaacccau   1080

cccugagaau ccaaaauucu ccgugccacc uaucacaccc cauccuaaag uaaggucagc   1140

uaaauaagcu aucgggccca uaccccgaaa auguugguua uacccuuccc guacuaauua   1200

auccccuggc ccaacccguc aucuacucua ccaucuuugc aggcacacuc aucacagcgc   1260

uaagcucgca cugauuuuuu accugaguag gccuagaaau aaacaugcua gcuuuuauuc   1320

caguucuaac caaaaaaaua aacccucuaa uagcuauccu cuucaacaau auacucuccg   1380
```

-continued

```
gacaaugaac cauaaccaau acuaccaauc aauacucauc auuaauaauc auaauagcua   1440
uagcaauaaa acuaggaaua gcccccuuuc acuucugagu cccagagguu acccaaggca   1500
ccccucugac auccggccug cuucuucuca caugacaaaa acuagccccc aucucaauca   1560
uauaccaaau cucucccuca cuaaacguaa gccuucuccu cacucucuca aucuuaucca   1620
ucauagcagg caguugaggu ggauuaaacc aaacccagcu acgcaaaauc uuagcauacu   1680
ccucaauuac ccacauagga ugaauaauag caguucuacc guacaacccu aacauaacca   1740
uucuuaauuu aacuauuuau auuauccuaa cuacuaccgc auuccuacua cucaacuuaa   1800
acuccagcac cacgacccua cuacuaucuc gcaccugaaa caagcuaaca ugacuaacac   1860
ccuuaauucc auccacccuc cucucccuag gaggccugcc cccgcuaacc ggcuuuuugc   1920
ccaaaugggc cauuaucgaa gaauucacaa aaaacaauag ccucaucauc cccaccauca   1980
uagccaccau cacccuccuu aaccucuacu ucuaccuacg ccuaaucuac uccaccucaa   2040
ucacacuacu ccccauaucu aacaacguaa aaauaaaaug acaguuugaa cauacaaaac   2100
ccaccccauu ccuccccaca cucaucgccc uuaccacgcu acuccuaccu aucuccccuu   2160
uuauacuaau aaucuuauag aaauuuaggu uaaauacaga ccaagagccu ucaaagcccu   2220
caguaaguug caauacuuaa uuucuguaac agcuaaggac ugcaaaaccc cacucugcau   2280
caacugaacg caaaucagcc acuuuaauua agcuaagccc uuacuagacc aaugggacuu   2340
aaacccacaa acacuuaguu aacagcuaag cacccuaauc aacuggcuuc aaucuacuuc   2400
ucccgccgcc gggaaaaaag gcgggagaag ccccggcagg uuugaagcug cuucuucgaa   2460
uuugcaauuc aauaugaaaa ucaccucgga gcugguaaaa agaggccuaa ccccugucuu   2520
uagauuuaca guccaaugcu ucacucagcc auuuuaccuc acccccacug auguucgccg   2580
accguugacu auucucuaca aaccacaaag acauuggaac acuauaccua uuauucggcg   2640
caugagcugg aguccuaggc acagcucuaa gccuccuuau ucgagccgag cugggccagc   2700
caggcaaccu ucuagguaac gaccacaucu acaacguuau cgucacagcc caugcauuug   2760
uaauaaucuu cuucauagua auacccauca uaaucggagg cuuuggcaac ugacuaguuc   2820
cccuaauaau cggugccccc gauauggcgu uuccccgcau aaacaacaua agcuucugac   2880
ucuuaccucc cucucuccua cuccugcucg caucugcuau aguggaggcc ggagcaggaa   2940
cagguugaac agucuacccu cccuuagcag ggaacuacuc ccacccugga gccuccguag   3000
accuaaccau cuucuccuua caccuagcag gugucuccuc uaucuuaggg gccaucaauu   3060
ucaucacaac aauuaucaau auaaaacccc cugccauaac ccaauaccaa acgccccucu   3120
ucgucugauc cguccuaauc acagcagucc uacuucuccu aucucuccca guccuagcug   3180
cuggcaucac uauacuacua acagaccgca accucaacac caccuucuuc gaccccgccg   3240
gaggaggaga ccccauucua uaccaacacc uauucugauu uuucggucac ccugaaguuu   3300
auauucuuau ccuaccaggc uucggaauaa ucucccauau uguaacuuac uacuccggaa   3360
aaaaagaacc auuuggauac auagguaugg ucugagcuau gauaucaauu ggcuuccuag   3420
gguuuaucgu gugagcacac cauauauuua caguaggaau agacguagac acacgagcau   3480
auuucaccuc cgcuaccaua aucaucgcua uccccaccgg cgucaaagua uuuagcugac   3540
ucgccacacu ccacggaagc aauaugaaau gaucugcugc agugcucuga gcccuaggau   3600
ucaucuuucu uuucaccgua gguggccuga cuggcauugu auuagcaaac ucaucacuag   3660
acaucguacu acacgacacg uacuacguug uagcccacuu ccacuauguc cuaucaauag   3720
```

-continued gagcuguauu ugccaucaua ggaggcuuca uucacugauu uccccuauuc ucaggcuaca 3780
cccuagacca aaccuacgcc aaaauccauu ucacuaucau auucaucggc guaaaucuaa 3840
cuuucuuccc acaacacuuu cucggccuau ccggaaugcc ccgacguuac ucggacuacc 3900
ccgaugcaua caccacauga aacauccuau caucuguagg cucauucauu ucucuaacag 3960
caguaauauu aauaauuuuc augauuugag aagccuucgc uucgaagcga aaaguccuaa 4020
uaguagaaga acccuccaua aaccuggagu gacuauaugg augcccccca cccuaccaca 4080
cauucgaaga acccguauac auaaaaucua gaggauc 4117

<210> SEQ ID NO 12
<211> LENGTH: 37
<212> TYPE: DNA
<213> ORGANISM: artificial
<220> FEATURE:
<223> OTHER INFORMATION: recombinant polynucleotide

<400> SEQUENCE: 12
ggaattctaa tacgactcac tatagggact gtagctc 37

<210> SEQ ID NO 13
<211> LENGTH: 32
<212> TYPE: DNA
<213> ORGANISM: artificial
<220> FEATURE:
<223> OTHER INFORMATION: recombinant polynucleotide

<400> SEQUENCE: 13
gggatccatg ctctaccaat tgagctacag tc 32

<210> SEQ ID NO 14
<211> LENGTH: 32
<212> TYPE: DNA
<213> ORGANISM: artificial
<220> FEATURE:
<223> OTHER INFORMATION: recombinant polynucleotide

<400> SEQUENCE: 14
gaagcttatg ctctaccaat tgagctacag tc 32

<210> SEQ ID NO 15
<211> LENGTH: 24
<212> TYPE: DNA
<213> ORGANISM: Homo sapiens

<400> SEQUENCE: 15
gcggatccat gttcgccgac cgtt 24

<210> SEQ ID NO 16
<211> LENGTH: 27
<212> TYPE: DNA
<213> ORGANISM: Homo sapiens

<400> SEQUENCE: 16
gcgaattcaa gaccctcatc aatagat 27

<210> SEQ ID NO 17
<211> LENGTH: 24
<212> TYPE: DNA
<213> ORGANISM: Homo sapiens

<400> SEQUENCE: 17
gcggatccat gacccaccaa tcac 24

-continued

```
<210> SEQ ID NO 18
<211> LENGTH: 24
<212> TYPE: DNA
<213> ORGANISM: Homo sapiens

<400> SEQUENCE: 18

atcgatcgag gcccatttga gtat                                          24


<210> SEQ ID NO 19
<211> LENGTH: 24
<212> TYPE: DNA
<213> ORGANISM: Homo sapiens

<400> SEQUENCE: 19

gcaagcttat acccatggcc aacc                                          24


<210> SEQ ID NO 20
<211> LENGTH: 23
<212> TYPE: DNA
<213> ORGANISM: Homo sapiens

<400> SEQUENCE: 20

gcgcggatcc tctagatttt atg                                           23
```

PROTEIN-CODING RNA TO CORRECT MITOCHONDRIAL DYSFUNCTION

This application claims the benefit of Indian Patent Application No. 2034/DEL/2008 filed on 28 Aug. 2008, and the text of the application "PROTEIN-CODING RNA TO CORRECT MITOCHONDRIAL DYSFUNCTION" is incorporated by reference in its entirety herewith.

FIELD OF THE INVENTION

The invention consists of compositions and methods for delivery of protein-coding RNAs (Pc RNAs) to correct mitochondrial dysfunction.

BACK GROUND OF THE INVENTION

The underlying defects in many human diseases [TABLE 1] [Taylor, R. W., & Turnbull, D. M. (2005) Mitochondrial DNA mutations in human disease. *Nature Rev Genet.* 6: 389-402] are in the functioning of the cellular energy-generating system of mitochondria. These defects are caused by mutations in mitochondrial genes, deletions and/or rearrangements of parts of the mitochondrial genome, or by mutations in nucleus-encoded genes specifying protein components of the oxidative phosphorylation (OX PHOS) pathway. Such mutations may be transmitted through the germ line or be somatic, and the disease is usually complex, with multi-tissue involvement.

In addition to the relatively rare disorders definitively linked to mitochondrial mutations [Taylor, R. W., & Turnbull, D. M. (2005) Mitochondrial DNA mutations in human disease. *Nature Rev Genet.* 6: 389-402, 23], mitochondrial dysfunction is associated with several more common diseases including Type 2 Diabetes mellitus (T2DM), metabolic syndrome, Parkinson's Disease, cardiomyopathies, certain cancers, sideroblastic anemia, etc. [Wilson, F. H., et al. (2004) A cluster of metabolic defects caused by mutation in a mitochondrial tRNA. *Science* 306: 1190-1194; Lowell, B. B. & Shulman, G. L. (2005) Mitochondrial dysfunction and Type 2 diabetes. *Science* 307: 384-387; Gottlieb, E., & Tomlinson, I. P. M. (2005) Mitochondrial tumor suppressors: a genetic and biochemical update. *Nature Rev Cancer* 5: 857-867]. Because of the ubiquitous presence and vital importance of mitochondria in the functioning of most cell, tissue and organ systems, correction of mitochondrial function is likely to have wide-ranging therapeutic benefits.

Mitochondrial mutations, particularly deletions of parts of the organellar genome, are known to accumulate in various tissues and organs of aged human and animal subjects who have not been diagnosed with any disease [Corral-Debrinski M. et al. (1992) Mitochondrial DNA deletions in human brain: regional variability and increase with advanced age. *Nature Genet.* 2: 324-329; Kopsidas, G., et al. (1998) An age-associated correlation between cellular bioenergy decline and mtDNA rearrangements in human skeletal muscle. *Mut Res* 421: 27-36; Waeler, R., et al. (2007) Engineering targeted viral vectors for gene therapy. *Nat. Rev. Genet.* 8: 573-587]. The deletions expand clonally in different regions of the tissue [Kopsidas, G., et al. (1998) An age-associated correlation between cellular bioenergy decline and mtDNA rearrangements in human skeletal muscle. *Mut Res* 421: 27-36]. Multiple deletions within the same aged subject have also been detected [Kopsidas, G., et al. (1998) An age-associated correlation between cellular bioenergy decline and mtDNA rearrangements in human skeletal muscle. *Mut Res* 421: 27-36]. There is no specific method for treating the myopathy, neuropathy and other debilitating symptoms of old age, which are likely to be caused principally by such deletions.

Therapy of a genetic defect requires transfer of corrective nucleic acids (RNA or DNA) into mitochondria of cells and tissues of the patient. There are several methods available for inducing uptake of nucleic acids into cells. These include chemical methods using divalent cations or other agents; physical methods such as biolistic missiles and electroporation; cationic liposomes; and viral vectors. The first three methods are inefficient, may be toxic to the host cells or organism, or technically inappropriate in a clinical setting. The viral vectors [Waeler, R., et al. (2007) Engineering targeted viral vectors for gene therapy. *Nat. Rev. Genet.* 8: 573-587] are efficient at delivery, but the viral genome is transported to the nucleus (with some exceptions, e.g. vaccinia virus, which replicates in the cytosol); no viruses are known that infect mitochondria. There is prior art on the delivery of small interfering (si)RNAs to the cytosol [e.g., ref. Klapdor, K., et al. (1997) *J. Neurosci. Meth.* 78: 49 Heidenreich, O. et al. (2008) RNAi modulation of MLL-AF4 and uses thereof. U.S. Pat. No. 7,361,752]. In this case, small double stranded RNA is delivered by liposomes or as lipid conjugates, but no protein-based carrier is involved.

There is currently no protocol available in the literature for efficiently transferring nucleic acids to correct mitochondrial genetic deficiencies in vivo [Kyriakouli, D. S. et al. (2008) Progress and prospects: gene therapy of mitochondrial DNA disease. *Gene Therapy* (2008) Advance Online publication, doi: 10.1038/gt.2008.91]. We have not observed any significant unassisted uptake of RNA into human mitochondria in vitro [Mahata, B., et al. (2005) Correction of translational defects in patient-derived mutant mitochondria by complex-mediated import of a cytoplasmic tRNA. *J. Biol. Chem.* 280: 5141-5144]. DNA was introduced into isolated mitochondria by electroporation [Collombet J. M., et al. (1997) Introduction of Plasmid DNA into isolated mitochondria by electroporation. A novel approach toward gene correction for mitochondrial disorders. *J. Biol. Chem.,* 272: 5342-5347], but in the absence of a demonstration of its efficacy on intracellular mitochondria, the genetic or therapeutic potential of electroporation is limited. DNA conjugated to a mitochondrial signal peptide was imported via protein import channels into isolated mitochondria [Vestweber, D., & Schatz, G. (1989) DNA-protein conjugates can enter mitochondria via the protein import pathway. *Nature* 338: 170-172], but there are no reports of the uptake of peptide-DNA conjugate on mitochondria within intact cells. Peptide Nucleic Acids (PNA) coupled to a lipophilic cation were taken up into the mitochondria of human cells; although PNA inhibited mutant DNA replication in vitro, it was without effect in intracellular mitochondria [Muratovska A., et al. (2001) Targeting peptide nucleic acid (PNA) oligomers to mitochondria within cells by conjugation to lipophilic cations: implications for mitochondrial DNA replication, expression and disease. *Nucl. Acids Res.,* 29: 1852-1863]. An alternative route, involving expression of the defective mitochondrial gene in the nucleus, translation of the mRNA in the cytosol, followed by import of the protein into mitochondria (allotopic expression), is has yielded conflicting results [Ojaimi, J., et al. (2002) An algal nucleus-encoded subunit of mitochondrial ATP synthase rescues a defect in the analogous human mitochondrial-encoded subunit. *Mol. Biol. Cell* 13: 3836-3844.

Bokori-Brown, M. & Holt, I. J. (2006) Expression of algal nuclear ATP synthase subunit 6 in human cells results in protein targeting to mitochondria but no assembly into ATP synthase. *Rejuvenation Res.* 9: 455-469].

The closest prior art to the invention is the delivery of signal-tagged oligonucleotides into cultured cells using a protein complex derived from *Leishmania tropica*; this resulted in inhibition of mitochondrial function in the treated cells [Mukherjee, S. et al. (2008) Targeted mRNA degradation by complex-mediated delivery of antisense RNAs to intracellular human mitochondria. *Hum. Mol. Genet.* 17: 1292-1298]. Such respiratory inhibition might be suitable as a cellular poison in certain clinical situations, but there is no report of functional RNAs to correct or repair a mitochondrial genetic defect.

Consequently, there is no specific treatment for mitochondrial genetic disorders such as MERRF, MELAS, NARP, KSS, etc. Non-specific treatments with creatine, coenzyme Q, etc. are without effect, resulting in debilitation or death of the patient, often at a very young age.

SUMMARY OF THE INVENTION

Accordingly, the present invention provides Pc RNA useful for the treatment of mitochondrial dysfunction, composition and method for preparing and using correctional RNA, with a carrier, administered to stimulate respiration of the cells, tissues, organs or the whole organism of normal or diseased subjects.

In an embodiment of the invention, provides Pc RNA, a recombinant polynucleotide segment having sequences selected from the group consisting of Seq ID no. 9, 10 and 11. In an embodiment the invention, provides the RNA is covalently linked to a signal tag, being a molecule that binds to a mitochondrial targeted carrier and is transported by it.

In yet another embodiment of the invention the signal-tagged correctional RNA is a protein-coding RNA (pcRNA) that encodes protein-coding genes of human mitochondria.

In yet another embodiment of the invention the signal-tagged correctional RNA is natural, synthetic or chemically modified at positions selected from the group comprising of bases, phosphodiester backbone, ribose sugars.

In yet another embodiment of the invention a composition useful for treating mitochondrial dysfunction comprising of correctional RNA with a signal tag, a carrier, and binding buffer.

In yet another embodiment of the invention the composition is useful for stimulating respiration of the cells, tissues, organs or the whole organism of normal or diseased subjects.

In yet another embodiment of the invention the correctional RNA is covalently linked to a signal tag, being a molecule that binds to a mitochondrially targeted carrier and is transported by it.

In yet another embodiment of the invention the signal tag is an oligonucleotide consisting of the D domain and containing the mitochondrial import signal of *Leishmania* tropica tRNATyr(GUA).

In yet another embodiment of the invention the signal-tagged correctional RNA is a protein-coding RNA (pcRNA) that encodes protein-coding genes of human mitochondria.

In yet another embodiment of the invention the signal-tagged correctional RNA is natural, synthetic or chemically modified at positions selected from the group comprising of bases, phosphodiester backbone, ribose sugars.

In yet another embodiment of the invention the signal-tagged pcRNA consists of a mixture of two or more pcRNAs encoding protein-coding genes of the human mitochondrial genome.

In yet another embodiment of the invention the signal-tagged pcRNA consists of a mixture of sequences selected from the group consisting of SEQ ID 9, 10, and 11.

In yet another embodiment of the invention the carrier is a complex of proteins selected from the group of sequences consisting of SeqID no. 1 to 8.

In yet another embodiment of the invention the carrier is a complex of proteins encoded by kinetoplastid protozoa selected from the group comprising of genera *Leishmania, Trypanosoma, Crithidia.*

In yet another embodiment of the invention the carrier complex is R6, consisting of proteins of SEQ ID 1, 3, 5, 6, 7, and 8; or R8, consisting of proteins of SEQ ID 1-8.

In yet another embodiment of the invention the carrier is administered separately or together with one or more of the signal-tagged correctional RNAs in various formulations.

In yet another embodiment of the invention the formulation is selected from the group comprising of aqueous solution, water or oil-based ointments, creams, suppositories, etc.

In yet another embodiment of the invention the route of administration is selected from the group consisting of local administration (including but not limited to intramuscular, intraocular, stereotaxy); systemic administration (including but not limited to intravenous, intraperitoneal; topical.

In yet another embodiment of the invention the subject is a human being.

In yet another embodiment of the invention the disease or physiological condition associated with mitochondrial dysfunction is selected from the group comprising of Myoclonic Epilepsy with Ragged Red Fibers (MERRF); Leigh Syndrome; Parkinson syndrome, Neuropathy and Myopathy; Multiple Symmetric Lipomatosis; Cardiomyopathy; Progressive External Opthalmoplegia (PEO) with monoclonus; Maternally Inherited Diabetes, with Deafness (MIDD); Mitochondrial Encephalopathy, Lactic Acidosis and Stroke (MELAS); Riboflavin sensitive myopathy; Isolated Cardiomyopathy; Maternally Inherited Diabetes, with Deafness (MIDD); Sudden Infant Death syndrome (SIDS); Maternal Deafness, whether or not syndromic; Late Onset Alzheimer's Disease; Metabolic Syndrome; Neuropathy, Ataxia, and Retinitis Pigmentosa [NARP]; Leber's Hereditary Optic Neuropathy (LHON); Myopathy, Exercise Intolerance, Encephalopathy, Lactic Acidemia; Kearns-Sayre Syndrome (KSS); maternal or sporadic Syndromic Deafness; Pearson's Syndrome; Sideroblastic Anemia; Wolfram Syndrome (Diabetes Insipidus, Diabetes Mellitus, Optic Atrophy, Deafness or DIDMOAD); Myopathy and external opthalmoplegia; Neuropathy, Gastro-Intestinal and Encephalopathy (MNGIE); Inclusion Body Myositis; polymyositis with $COX^-$ muscle fibers; tissue injury caused by factors including but not limited to burn, laceration, chemicals, and infectious disease.

In yet another embodiment of the invention a method of delivering the composition wherein the intracellular organelle to which delivered is a mitochondrion.

In yet another embodiment of the invention wherein the Pc-RNA is introduced into the eukaryotic cell by a method selected from the group consisting of electroporation, DEAE Dextran transfection, calcium phosphate transfection, cationic liposome fusion, protoplast fusion, creation of an in vivo electrical field, DNA-coated microprojectile bombardment, injection with a recombinant replication-defective virus, homologous recombination, ex vivo gene therapy, a viral vector, and naked DNA transfer.

In yet another embodiment of the invention the eukaryotic cell to which delivered is a mammalian cell.

In yet another embodiment of the invention the cell to which delivered is a human cell. In yet another embodiment of the invention when applied to a mitochondrial disorder that is associated with a mutation in mtDNA.

In yet another embodiment of the invention a method for correcting a phenotypic deficiency in a mammal that results from a mutation in a peptide-encoding sequence of the mammal's mitochondrial DNA (mtDNA), In yet another embodiment of the invention a eukaryotic cell transformed by a Pc RNA in combination with a carrier that is useful for introducing a functional Pc RNA encoded by nuclear, mitochondrial or chloroplast DNA into an intracellular organelle, wherein the eukaryotic cell is of animal, plant or protist.origin and the expression vector comprises: a non-nuclear nucleic acid sequence encoding the peptide, wherein the nucleic acid sequence is compatible with the universal genetic code; and a nucleic acid sequence encoding an organelle-targeting signal.

In yet another embodiment of the invention the eukaryotic cell expresses the RNA.

In yet another embodiment of the invention use of the composition for treatment of a mitochondrial dysfunction related disorder In yet another embodiment of the invention use of Pc-RNA with or without carrier complex for treatment of a mitochondrial dysfunction related disorder mitochondrial dysfunction related disorder a kit for treating mitochondrial dysfunction wherein the kit consists of the carrier (component A), Pc RNA (component B) and binding buffer.

BRIEF DESCRIPTION OF THE DRAWINGS

FIG. 3 depicting the sequences of pcRNAs 1, 2 and 3 (SEQ ID NO:9, SEQ ID NO:10 and SEQ ID NO:11, respectively). The signal tags are indicated in red, the human mitochondrial protein-coding sequences in black, and the tRNA sequences in blue. Gene identities are shown in text boxes. Key: black letters: protein-coding genes (labeled in boxes); blue, intergenic spacer, tRNA genes and linkers; red, D arm sequence; ppp, 5'-triphosphate end of RNA transcript; green highlight, start codons; red highlight, stop codons (incomplete stop codons of mitochondrial mRNAs are completed by poly A addition to the 3'-end).

DETAILED DESCRIPTION OF THE INVENTION

Figure 1:
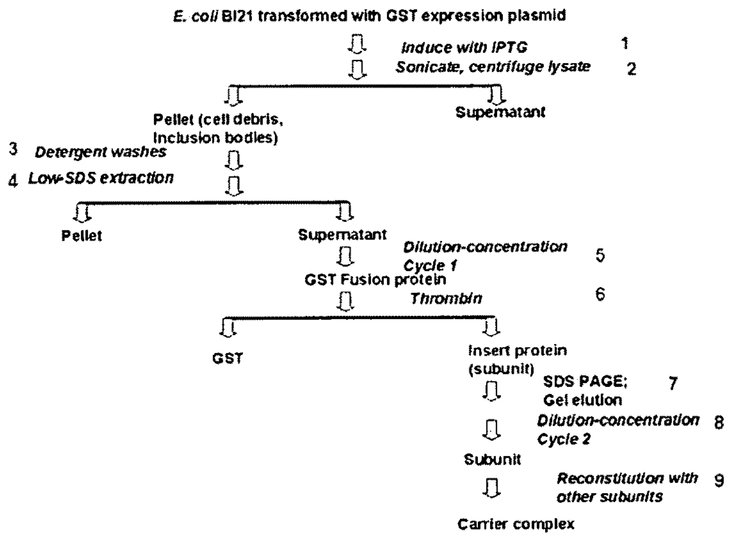
FIG. 1 is a flow chart showing preparation of recombinant subunits of carrier complexes.

Accordingly, the present invention discloses a recombinant polynucleotide segment particularly comprising a sequence set forth in SEQ ID NO:9, SEQ ID NO:10 or SEQ ID NO:11 and the sequence operably linked to a signal tag. A signal tag is a short oligoribonucleotide sequence that binds to the carrier complex and is transported by it across cellular and mitochondrial membranes. The signal tag may consist of part or whole of the natural substrate (i.e. tRNA) for the carrier. It may be synthesized chemically or by template-directed transcription by RNA polymerase. The signal is covalently attached to the pcRNA. The site of attachment may be the 5'- or 3'-end of the pcRNA. The signal tag may be chemically modified in the phosphodiester backbone, in the sugar moieties or in the bases to improve stability or efficacy.

The recombinant polynucleotide segment is the sequence disclosed in SEQ ID NO:9 or the recombinant polynucleotide segment, is the sequence disclosed in SEQ ID NO:10 or the recombinant polynucleotide segment, is the sequence disclosed in SEQ ID NO:11 or all three sequences in a combination.

Further, the invention comprises a vector with the recombinant polynucleotide segment a non-nuclear nucleic acid sequence encoding the peptide. The vector construct is performed according to standard procedures The isolated host cell transformed with the vector is of animal, plant or prokaryotic origin. Preferably, the host cell is a mammalian cell, an insect cell (e.g., sf9 or HiFive) or an *E. coli* cell.

Another aspect of the invention is for a process for producing at least one human mitochondrial protein intra-cellularly, the process comprising the steps of culturing the isolated host cell of claim 4 in the presence of a group of proteins comprising SEQ ID NOS: 1, 3, 5, 6, 7 and 8 under conditions sufficient for the production of at least one human mitochondrial protein.

The process of the invention includes a group of proteins of SEQ ID NOS: 1, 3, 5, 6, 7 and 8 which is defined as R6 protein. The carrier protein also is of a group of proteins of SEQ ID NOS: 1-8 and is defined as R8.

An aspect of the invention is a recombinant polynucleotide comprising a sequence set forth in SEQ ID NO:12 and a complementary strand thereof selected from the group consisting of SEQ ID NO:13 and SEQ ID NO:14.

Another aspect of the invention is a composition comprising a polyribonucleotide sequence as disclosed in SEQ ID NO:9, SEQ ID NO:10 or SEQ ID NO:11 or a mixture thereof.

The composition of the invention is a polyribonucleotide sequences as disclosed in SEQ ID NO:9, SEQ ID NO:10 and SEQ ID 11.

The composition further comprises a carrier that is a protein or a group of proteins for transporting the polyribonucleotide sequence or the mixture thereof across cellular and mitochondrial membranes.

The carrier proteins of the composition are of SEQ ID NOS: 1, 3, 5, 6, 7 and 8; and of group of proteins of SEQ ID NOS: 1-8.

The composition further comprises a binding buffer.

Another aspect of the invention is a method of treating a disease or physiological condition associated with mitochondrial dysfunction in a mammal comprising administering a composition comprising an amount of a polyribonucleotide sequence set forth in SEQ ID NO:9, SEQ ID NO:10 or SEQ ID NO:11 or a mixture thereof, a carrier comprising a group of proteins comprising SEQ ID NOS: 1, 3, 5, 6, 7 and 8 and a binding buffer sufficient for the treatment of the disease or physiological condition associated with mitochondrial dysfunction.

The carrier is administered separately together with the polyribonucleotide sequence or mixture thereof in a pharmaceutically acceptable formulation.

For the said method of treatment, the formulation is selected from the group comprising of an aqueous solution and water- or oil-based ointments, creams or suppositories.

For the said method of treatment, the composition is administered intramuscularly, intraocularly, stereotactically, intravenous, intraperitoneally or topically.

The method of treatment is in mammals, and the said mammal is a human.

An aspect of the invention for the method of treatment of disease or physiological condition associated with mitochondrial dysfunction is selected from the group comprising of Myoclonic Epilepsy with Ragged Red Fibers (MERRF), Leigh Syndrome, Parkinson syndrome, Neuropathy and Myopathy, Multiple Symmetric Lipomatosis, Cardiomyopathy, Progressive External Opthalmoplegia (PEO) with monoclonus, Maternally Inherited Diabetes with Deafness (MIDD), Mitochondrial Encephalopathy, Lactic Acidosis and Stroke (MELAS), Riboflavin sensitive myopathy, Isolated Cardiomyopathy, Maternally Inherited Diabetes with Deafness (MIDD), Sudden Infant Death syndrome (SIDS), Maternal Deafness, Late Onset Alzheimer's Disease, Metabolic Syndrome, Neuropathy, Ataxia and Retinitis Pigmentosa (NARP), Leber's Hereditary Optic Neuropathy (LHON), Myopathy, Exercise Intolerance, Encephalopathy, Lactic Acidemia, Kearns-Sayre Syndrome (KSS), maternal or sporadic Syndromic Deafness, Pearson's Syndrome, Sideroblastic Anemia, Wolfram Syndrome (Diabetes Insipidus, Diabetes Mellitus, Optic Atrophy, Deafness or DIDMOAD), Myopathy and external opthalmoplegia; Neuropathy, Gastro-Intestinal and Encephalopathy (MNGIE), Inclusion Body Myositis, polymyositis with $COX^-$ muscle fibers and tissue injury.

In one aspect of the invention, a method of preparing a composition involving the following steps is provided: expressing coding sequences for subunits R6 (SEQ ID NOS: 1, 3, 5, 6, 7 and 8) and/or R8 (SEQ ID NOS: 1-8) in an *E. coli* strain and isolating the essentially pure mixture of subunits R6 and R8 thereby obtaining the carrier or carrier protein complex (either is a component A), wherein the carrier protein is expressed in an *E. coli* strain and purified; preparing a recombinant polyribonucleotide segments each comprising a sequence set forth in SEQ ID NO:9, SEQ ID NO:10 or SEQ ID NO:11 by using a recombinant polynucleotide comprising a sequence set forth in SEQ ID NO:12 and a complementary strand thereof selected from the group consisting of SEQ ID NO:13 and SEQ ID NO:14 as starting material to obtain full-length SEQ ID NO:9, SEQ ID NO:10 and SEQ ID NO:11 (component B); and mixing components A and B in the presence of a binding buffer and incubating the mixture for a time sufficient to form the composition containing a complex of components A and B.

In a particularly preferred embodiment of the invention, a method of preparation of carrier (component A), preparation of composition of RNA (Component B) and formation of the RNP complex is carried out as follows for preparing the composition Preparation of Carrier (Component A):

a) Expressing the coding sequence of the cloned gene encoding subunits of R6 and R8 which is inserted downstream of the Glutathione S-transferase (GST) gene of plasmid vector pGEX4T-1 wherein the recombinant plasmid is transferred to the expression strain *E. coli* BL21,
b) disrupting the cells obtained in step a by ultrasonication and the particulate fraction, containing most of the expressed protein, is isolated by centrifugation,
c) extracting the pellet obtained in step b with detergent to solubilize impurities by known methods,
d) solubilizing the expressed protein obtained in step c with a low concentration of anionic detergent by known methods,
e) diluting 5-10 fold, the expressed protein solution obtained in step d with TETN buffer then concentrated by centrifugal ultrafiltration,
f) digesting the concentrated fusion protein obtained in step e with thrombin to separate the GST tag from the expressed insert protein,
g) resolving the expressed protein obtained in step f from GST by SDS polyacrylamide gel electrophoresis (PAGE), excised and eluted,
h) diluting and concentrating the eluate obtained in step g as done in step e,
i) combining and incubating equal amounts of the recombinant subunits obtained in step h to form the carrier complex,
j) aliquoting the reconstituted carrier obtained in step I storing at −70° C., and thawing just before use (component A).

Preparation of Composition of RNA (Component B):

annealing together two synthetic oligonucleotides having SEQ ID 12 and 13; or SEQ ID 12 and 14 to form a partially double-stranded DNA,
converting the partially double-stranded intermediate obtained in step k to fully double stranded form by gap-filling with the Klenow fragment of *E. coli* DNA polymerase I,
amplifying the protein coding sequences to be tagged from human mitochondrial DNA by polymerase chain reaction (PCR) using primer pairs having SEQ ID 15-20,
digesting the amplified protein coding fragment obtained in step m with the appropriate restriction enzymes to liberate cohesive ends.
Attaching each amplified protein-coding DNA obtained in step m to the promoter tag cassette with DNA ligase,
amplifying the ligation product obtained in step o by PCR using flanking primers to generate the transcription template containing the T7 promoter, the signal tag followed by the protein-coding sequence,
transcribing the template obtained in step p in vitro with T7 RNA polymerase to yield full-length tagged pcRNA, recovering the pcRNA obtained in step q by ethanol precipitation, suspended in water, aliquoted, lyophilized, and stored at −70° C. (component B).

Preparation of Binding Buffer:

An aqueous solution of Tris-HCl, about 20 mmol/li; $MgCl_2$, about 20 mmol/li; dithiothreitol, about 2 mol/li; NaCl, about 200 mmol/li; glycerol, about 10%. Total volume: 10 μL.

Formation of the RNP Complex

Component A obtained in step i is added to reconstituted component B obtained in step ii and the mixture is incubated on ice for 30 min to form the RNP complex.

The invention also discloses a kit with two active components A and B having a correctional RNA and carrier protein for transporting the RNA across cell and mitochondrial membranes, and a binding buffer, which are combined prior to use to form the ribonucleoprotein (RNP) complex. The RNP complex is administered through a suitable route. Further the use of the kit is for a diagnosis for screening mitochondrial dysfunction, using the components provided in the kit.

Carrier Protein:

The carrier is a complex of proteins derived from *Leishmania tropica* that binds specifically and with high affinity to oligonucleotide sequences known as import signals, which are normally present on various transfer RNA (tRNA) molecules and which, when attached to other RNA or DNA molecules, allows such molecules to be recognized by the complex [Mukherjee, S., Basu, S., Home, P., Dhar, G., & Adhya, S. (2007) Necessary and sufficient factors for import of tRNA into the kinetoplast-mitochondrion. *EMBO Rep.,* 8: 589-595.]. Secondly, this complex is taken up by mammalian cells and targeted to mitochondria [Mahata B., Mukherjee, S., Mishra, S., Bandyopadhyay, A., & Adhya, S. (2006) Functional delivery of a cytosolic tRNA into mutant mitochondria of human cells. *Science.* 314: 471-474.]. Third, the bound RNA is then imported into the mitochondria. Finally, the delivered RNA is functional within the mitochondria.

Figure 5:
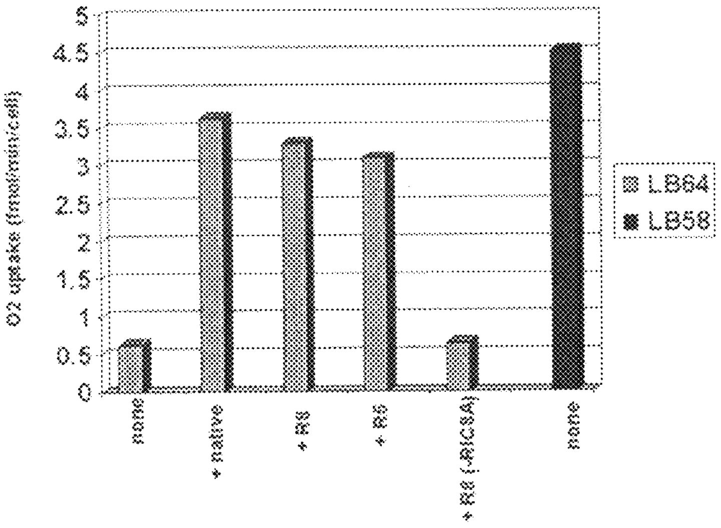
FIG. 5 is a representation of the effect of signal-tagged pcRNA-1-R8 combination on respiration of cybrid FLP32.39 (FLP) carrying a 1.9-kb mitochondrial deletion.

Composition of Carrier:

The carrier consists of a minimal core of six proteins (hereinafter termed R6) derived from *Leishmania tropica* strain UR6; or the nuclear core of eight proteins (R8), wherein R8 contains all the polypeptides of R6 plus 2 other proteins also derived from *Leishmania tropica* strain UR6; or the native form consisting of R8 plus three other proteins encoded by *Leishmania* mitochondria [Mukherjee, S., Basu, S., Home, P., Dhar, G., & Adhya, S. (2007) Necessary and sufficient factors for import of tRNA into the kinetoplast-mitochondrion. *EMBO Rep.,* 8: 589-595]. The three forms have similar biological activity (FIG. 5). Thus, each of R6, R8 and native forms contains a group of proteins and is referred to herein as a carrier. However, a given protein in any given group can be used as a carrier protein with or without further modifications either by recombinant means or through synthetic means. A mixture of R6 and R8 subunits is also sometimes referred to herein as carrier complex.

All of these proteins are major functional subunits of the *Leishmania tropica* RNA Import Complex [Mukherjee, S., Basu, S., Home, P., Dhar, G., & Adhya, S. (2007) Necessary and sufficient factors for import of tRNA into the kinetoplast-mitochondrion. *EMBO Rep.,* 8: 589-595]. RIC1, RIC3, RIC4A, RIC5, RIC6, RIC8A, RIC8B and RIC9 [SEQ ID 1-8; TABLE 1] are nucleus-encoded and all except RIC3 and RIC5 are essential for RNA transfer.

TABLE 1

Identities of carrier complex subunits

| Subunit | Sequence id | Gene id (LeishDB) | Database annotation | Protein sequence |
|---|---|---|---|---|
| RIC1 | 1 | LmjF05.0500 | ATPase alpha subunit | MRRFVAQYVAPAMGRLASTAAAGKSAAPGQKSFFKAT<br>EMIGYVHSIDGTIATLIPAPGNP<br>GVAYNTIIMIQVSPTTFAAGLVFNLEKDGRIGIILMDNITE<br>VQSGQKVMATGKLLYIPVG<br>AGVLGKVVNPLGHEVPVGLLTRSRALLESEQTLGKVDA<br>GAPNIVSRSPVNYNLLTGFKAV<br>DTMIPIGRGQRELIVGDRQTGKTSIAVSTIINQVRSNQQIL<br>SKNAVISIYVSIGQRCSNV<br>ARIHRLLRSYGALRYTTVMAATAAEPAGLQYLAPYSGV<br>TMGEYFMNRGRHCLCVYDDLSK<br>QAVAYRQISLLLRRPPGREAYPGDVFYLHSRLLERAAML<br>SPGKGGGSVTALPIVETLSND<br>VTAYIVTNVISITDGQIYLDTKLFTGGQRPAVNIGLSVSR<br>VGSSAQNVAMKAVAGKLKGI<br>LAEYRKLAADSVGGSQVQTVPMIRGARFVALFNQKNPS<br>FFMNALVSLYACLNGYLDDVKV<br>NYAKLYEYLLVNKDLSVMYGTATNKFFYMYVQQLNY<br>VIRFFTLNHPILNAEVEEMLKQHT<br>HLFLQHYQSKMNAIKTEKEIKALKNLLYSCKRAV |
| RIC3 | 2 | LmjF21.0340 | mitochondrial processing peptidase alpha subunit, putative | MLRATSRLGIYEYQFGQPSLKNAFSTRITPAAKARSPGA<br>VQSTKLTNGVRVVSHDLDGPV<br>TSIGVYADAGPKYDPIATPGLSYVMRFALQTSNMDSSLF<br>QIDRTMRSTGNAYGHGEVCKR<br>YLSWKAEGRRDMWEKPFEMLATGVVAPRFHESDIERFR<br>DTMDNQLEEMRWQNPREYAIDQ<br>LETVAFYKEPLGAPRMVPRIANDRCSHKALLDHWAANF<br>QPSRIVLAGVNVPHDALIAAYE<br>KLPYKHSAEAPHHARAAAPKLSHSNEVAQFYAGRQNVE<br>YESRAAVMGTMPDMQAEVIGAV<br>GVPTHGRDEGATQYATALVTREIYEEAMRSAHGSRAGS<br>EHYGAQVFYRPYSSAGLIGYTV<br>RGAPAEVAKMLQVASSAFPAAVDEAAVKRAAHCAHVR |

TABLE 1-continued

Identities of carrier complex subunits

| Sub-unit | Sequence id | Gene id (LeishDB) | Database annotation | Protein sequence |
|---|---|---|---|---|
| | | | | LLHDQVEMTRDYCDFLATSPNSV<br>EELVQAISGVTKANVEEAMKKMVAQKPATYATGDSFTF<br>PMVASLKHA |
| RIC4 A | 3 | LmjF07. 1110 | hypothetical protein, unknown function | MSLKHVASFGAVGVLSVVGMLGGRRWHRVELRRAELN<br>EEYTKLMNEMRTFNEKRLTRDERLAAKEAEAKVTAETV<br>DILWSDRLARYAQVNKDLHAYLAALPEAIGVLKGLSNH<br>YRYMSEEMPKFTGFDIACSKMHNLALMLEHGKAVGIER<br>VAATVQAMFVAEPLVQAVCTSILAAPAPPHPSSIAAASA<br>AFTFCMEELDRAVGTVAMRYAAALEEPPNATPGILSDS<br>VRKLVSMMRTDTLCKGQRQLAERRRDLERTLRRAQRQ<br>LHTEEDIRAALDYTRELDQHLQAAAPRRTDLLLSSPSRK<br>DNFLAAVRSDSEVKKAIQQIDLWRDSATTFLVHRQAED<br>ALQSYYFLLAETLTAVNELK |
| RIC 5 | 4 | LmjF12. 0670 | cyto-chrome oxidase subunit 4 | MLTRRAVSSAVGAAMVTSSSVSMQRRYDHDRWYGHA<br>LELDTHNYKFNGEPPSWMKTRAKTEETSFAKSVLPHIDF<br>ASSYECLLFDADRLNTNLNRKEFGNEIKYRLEKQANTV<br>ARAQQLLRDKKAGTGPDAEKVENTLIARIFDEEHVQAE<br>MKYVKCIRANELAEDNRLDILPGGSPNSLREKTRWNLN<br>TELHPADRAEIGARLTAWLPEKYHIVYFDDFQTVAAND<br>ATARKEMLEIVESVQKEYTAEAKEGGYESDLKEAVAEL<br>MDDVDPTRTITMEAIKSCKDLQQLEDWSRQVHEYNGD<br>DRIIAIYARAAEITKNVEHQALVRQMREWRKLATKNES<br>KL |
| RIC 6 | 5 | LmjF35. 1540 | reiske iron-sulfur protein precursor, putative | MFRRSFISAFQATRPARVSLVFKQLEGNMPLTKKDKPVD<br>SWSDEFMKPPQSAEMTKKYGRYAKYSDPALCDVDTSD<br>EVVLNTYPEGAPQGRIEATAGVALKDYDASMWDEEFFR<br>KHILKPKLADDMEDRARVTDYALNSAMLGFVILMARY<br>AVLPLWYVGQPAMSMVGQMNIEAEVGELDERQCTTVV<br>WGKPVFVYRRSARQMKEVMETPLSALKDPETDEARFPD<br>HRDKAVVIAICTHLGCVPIPNEGLFNGFFCPCHGSHYDPS<br>GRIRQGPAPLNLEVPPYRWIDDHTIYMGKL |
| RIC8 A | 6 | LmjF35. 0100 | hypothetical protein, conserved | MMKPTSPNFMAQGIWAGFRYYIGHFFYPNMYREFLSVQ<br>NAHKVERALRLQKAIKANKIDY<br>RALLALPVTDHAHPYKMEYPWEKVMQSDARDLGFYGK<br>WYASKMMCFYEGLQFHKWGCLQDDLINAHGWWNRA<br>ARTRAPKDKVVHGDRRVMRARVLKDKYIYEPKDRWV<br>HPVDNVAYFGPYVMMVADEWEEKWGFFAGQEVEY |
| RIC8 B | 7 | LmjF04. 0630 | ubiquinol cyto-chrome c reductase subunit 6b | MTMNFGNMTLGGAMATFGGQSNPMCNYTSPLAKKFV<br>YKEVGKVYYPLRRHVFRTKVRTAAEIR<br>FNEIVKRYMKEKMTFKRGCYAATITNTVELDHMGSIIPK<br>DEYEVKRLTSYMTSKKMSNDYKKHMQELWTRVLFVCE<br>STNLVGVTENAMHQNSRPGTDEEFMSLIWYSSFVTTLM<br>AFVVTLCIWWYRYG |
| RIC9 | 8 | LmjF21. 1710 | | MPHEDHKKYRVQREDLPAMPHFSDFNDPRFCGTTNKQ<br>KNGILAYYQWLHCIGNWGEEHSM<br>CKKMRWYVERMMHETWLEKWEEKRALGHFDHTVLY<br>GVKPWKEFEPLYQPVKKNRKGAYEYWLDRDFEPLYDV<br>DAADWRERAPILHDMFVLGKKPVSE |

The sequences of the *L. tropica* genes and proteins are available in the *Leishmania major* sequence database. The *Leishmania* protein sequences are nearly or completely identical to their homologues in other protozoa of the Order Kinetoplatidae, including *L. major, L. donovani, Trypanosoma brucei* and *Trypanosome cruzi*. Thus R6 or R8 or any other complex or sub-complex reconstituted from proteins encoded by any or all of these organisms are functionally equivalent, to be considered within the scope of this invention.

The invention specifically uses R6, consisting of RIC1, RIC4A, RIC6, RIC8A, RIC8B and RIC9; or R8, consisting of all of the subunits of R6 plus RIC3 and RIC5.

Preparation of Carrier (Component A):

The native form is purified from inner mitochondrial membranes of *L. tropica* by published procedures [Bhattacharya S. N., Chatterjee, S., Goswami, S., Tripathi, G., Dey, S. N., & Adhya, S. (2003) "Ping pong" interactions between mitochondrial tRNA import receptors within a multiprotein complex. *Mol. Cell. Biol.,* 23: 5217-5224]. In the present invention, it is preferred to take an alternative route, consisting of protein expression by recombinant DNA techniques combined with protein purification methods [Goswami, S., Dhar, G., Mukherjee, S., Mahata, B., Chatterjee, S., Home, P., & Adhya, S. (2006) A bi-functional tRNA import receptor from *Leishmania* mitochondria. *Proc. Natl. Acad. Sci. U.S.A.,* 103: 8354-8359].

One advantage of the present method is that the carrier complex is simple to prepare, with biochemically defined components, is suitable for upscaling and automation, yields complexes of greater purity, and avoids the expenses and hazards associated with handling large amounts of protozoa with infective potential.

The genes encoding the subunits of R6 and R8 are separately expressed in *E. coli*, purified and combined in vitro to reconstitute the carrier complex [FIG. 1].

1) The coding sequence of the cloned gene encoding each subunit has been inserted downstream of the Glutathione S-transferase (GST) gene of plasmid vector pGEX4T-1 (GE Life Sciences) and the recombinant plasmids transferred to the expression strain *E. coli* BL21. The plasmid-bearing strains are cultured and expression induced with isopropyl β-thio galactoside (IPTG).
2) The cells are disrupted by ultrasonication and the particulate fraction, containing most of the expressed protein, is isolated by centrifugation.
3) The pellet is extracted with detergent (sodium deoxycholate followed by Triton X-100) to solubilize impurities.
4) The expressed protein is solubilized with a low concentration of anionic detergent (0.2% sodium dodecyl sulfate).
5) The expressed protein solution is diluted 5-10 fold with TETN buffer [Goswami, S., Dhar, G., Mukherjee, S., Mahata, B., Chatterjee, S., Home, P., & Adhya, S. (2006) A bi-functional tRNA import receptor from *Leishmania* mitochondria. *Proc. Natl. Acad. Sci. U.S.A.*, 103: 8354-8359], then concentrated by centrifugal ultrafiltration.
6) The concentrated fusion protein is digested with thrombin to separate the GST tag from the expressed insert protein.
7) The expressed protein is resolved from GST by SDS polyacrylamide gel electrophoresis (PAGE), excised and eluted.
8) The eluate is subjected to dilution and concentration as in step 5.
9) Equal amounts of the recombinant subunits are combined and incubated to form the carrier complex.

The reconstituted carrier can be stored in aliquots at −70° C., and thawed just before use (component A).

Details of the expression and purification protocol for small-scale purification are available [Goswami, S., Dhar, G., Mukherjee, S., Mahata, B., Chatterjee, S., Home, P., & Adhya, S. (2006) A bi-functional tRNA import receptor from *Leishmania* mitochondria. *Proc. Natl. Acad. Sci. U.S.A.*, 103: 8354-8359]. The procedure may be scaled up with suitable modifications. Other methods of protein expression and purification besides the above system, and of reconstitution, are expected to yield carrier complexes of equivalent biological activity to R6 and R8, and are therefore considered to be within the scope of this invention.

Figure 2:
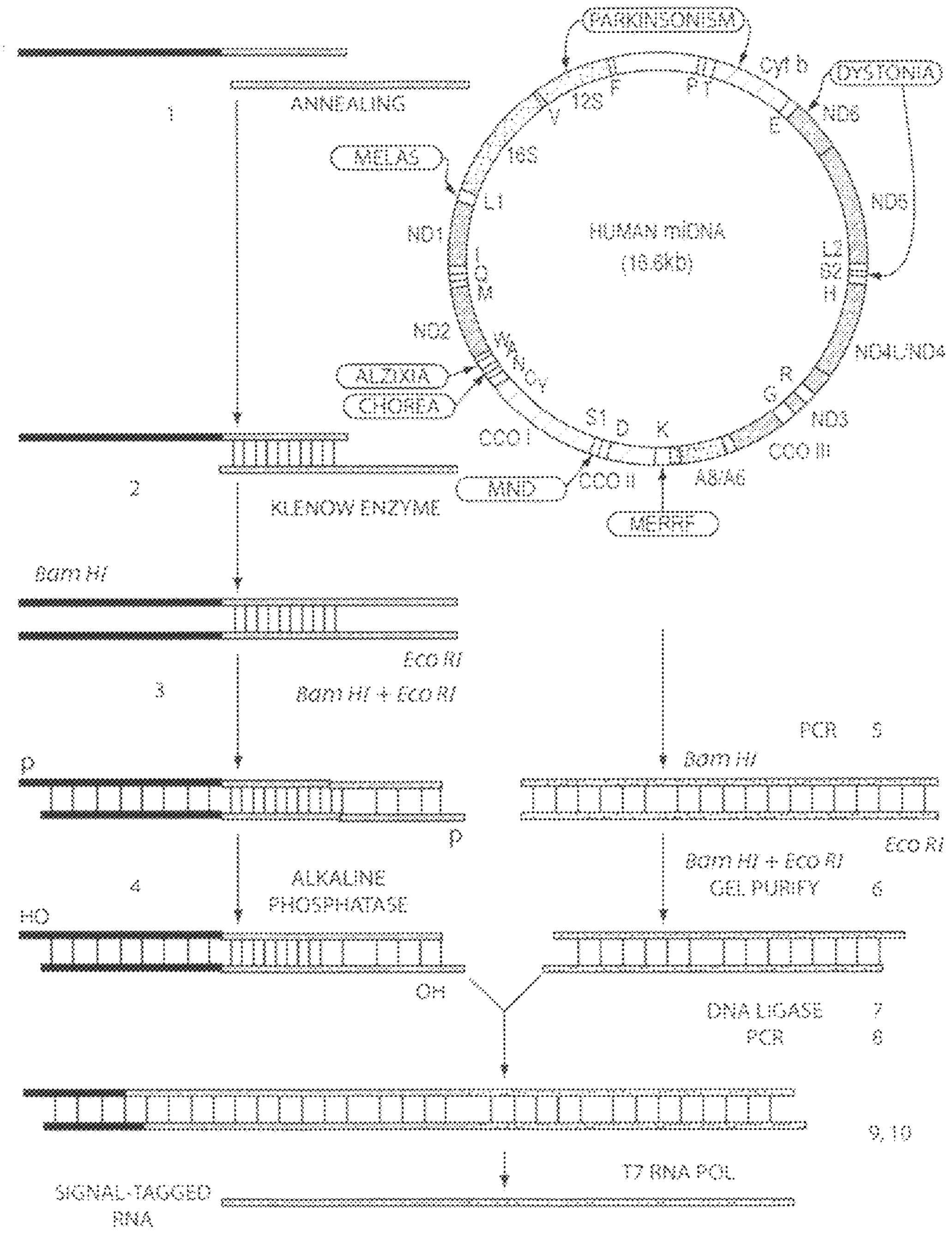
FIG. 2 is schematic drawing showing the preparation of signal-tagged protein-coding RNA.

Composition of RNA (Component B):

The invention uses signal-tagged protein-coding (pc) RNAs [FIG. 2] encoded by the human mitochondrial genome.

A signal tag is a short oligoribonucleotide sequence that binds to the carrier complex and is transported by it across cellular and mitochondrial membranes.

The signal tag may consist of part or whole of the natural substrate (i.e. tRNA) for the carrier. It may be synthesized chemically or by template-directed transcription by RNA polymerase. The signal is covalently attached to the pcRNA. The site of attachment may be the 5'- or 3'-end of the pcRNA. The signal tag may be chemically modified in the phosphodiester backbone, in the sugar moieties or in the bases to improve stability or efficacy.

The invention employs a signal tag derived from the D domain of the *Leishmania tropica* tRNATyr(UGA) [Mahapatra, S., Ghosh, S., Bera, S. K., Ghosh, T., Das, A., & Adhya, S. (1998) The D arm of $tRNA^{Tyr}$ is necessary and sufficient for import into *Leishmania* mitochondria in vitro. *Nucl. Acids Res.* 26: 2037-2041] [FIG. 2]. However, many other tRNA sequences are known to be natural or artificial substrates for the carrier complex, and many other tRNAs from other kinetoplastid protozoa are identical in sequence to the corresponding *Leishmania* tRNAs. Additionally, the complex is known to interact with human tRNAs [Mahata B., Mukherjee, S., Mishra, S., Bandyopadhyay, A., & Adhya, S. (2006) Functional delivery of a cytosolic tRNA into mutant mitochondria of human cells. *Science.* 314: 471-474]. Thus, in principle, any of a large number of sequences from different organisms may serve as signal tag.

All such variants are derived from the original concept of covalent tagging of import signals, and therefore fall within the scope of the invention.

In particular, the invention employs the signal tag derived from the D domain of the *Leishmania tropica* tRNATyr (UGA) covalently attached at the 5'-end of pcRNAs 1, 2 and 3 [SEQ ID 9, 10 AND 11, respectively] [FIG. 3].

In the invention, the signal tag is covalently attached to one or more pcRNAs corresponding to mitochondrial genes. These pcRNAs, delivered to mitochondria, will provide translation templates for synthesis of normal mitochondrial proteins to replace missing or defective ones arising from mitochondrial mutation/deletion.

Figure 4:
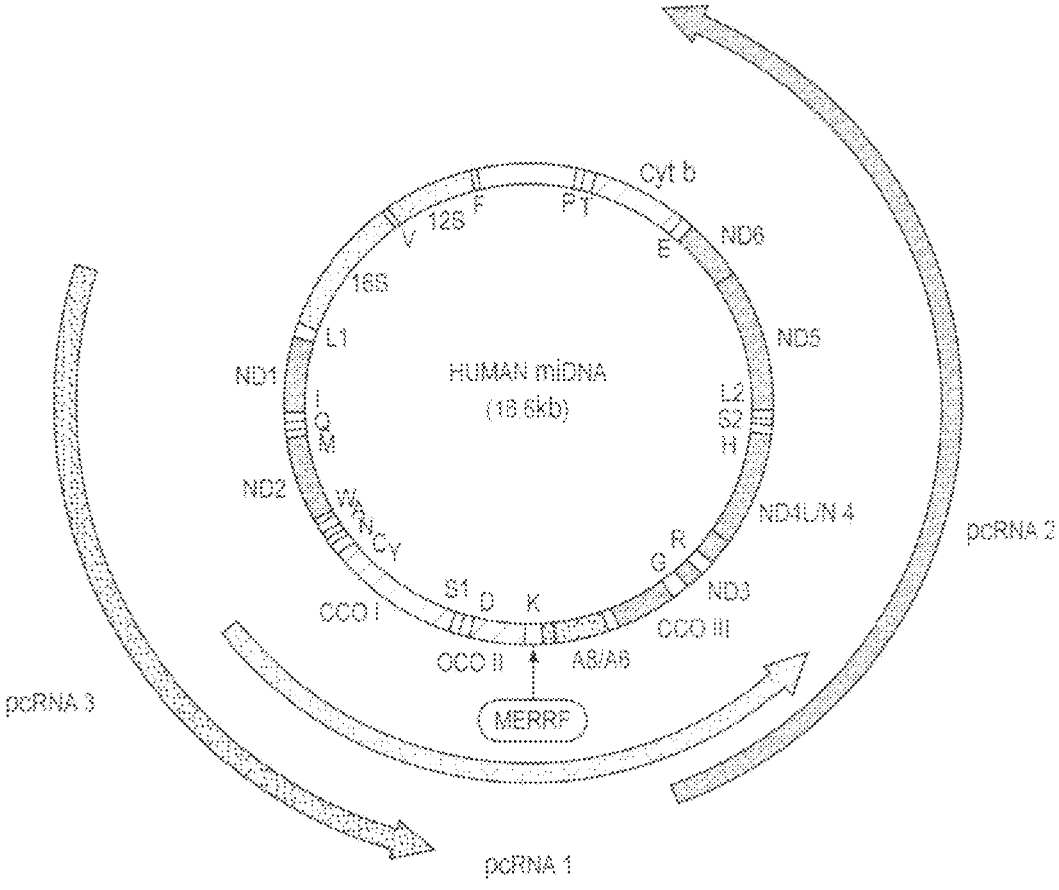
FIG. 4 illustrates the maps of pcRNA 1, 2 and 3 (red, blue and green) on the human mitochondrial genome.

The sequences of the pcRNAs 1, 2 and 3 are shown in FIG. 3. The signal tag is attached to each of the three different pcRNAs [SEQ ID 9-11; FIG. 3]. Each of these RNAs contains multiple human mitochondrial protein-coding sequences. In combination, the three RNAs cover the entire protein-coding part of the human mitochondrial genome except ND6 (which is coded by the opposite strand of mitochondrial DNA and is therefore not present in the transcript pcRNAs) [FIG. 4]. The human mitochondrial genome sequence is in the public domain [Anderson, S., et al. (1981) Sequence and organization of the human mitochondrial genome. *Nature,* 290: 457-464], but the pcRNAs are novel in containing the 5'-tag of *Leishmania* origin.

Genome-wide coverage is essential for full functionality in cases where the exact nature of the mitochondrial mutation is unknown, or heterogeneity in the mutation pool is known or suspected, for example, in aged individuals who display a variety of mitochondrial deletions. Genome-wide coverage can theoretically be achieved by any combination of RNAs containing one or more protein-coding sequences. Variations in the composition of pcRNAs are considered to be within the conceptual framework of genome-wide coverage, and therefore within the scope of the invention.

Preparation of Signal Tagged pcRNA

The signal-tagged pcRNAs are synthesized as follows (FIG. 2).

(1) Two synthetic oligonucleotides (ODN) [SEQ ID 12 and 13; or SEQ ID 12 and 14][TABLE 3] are annealed together to form a partially double-stranded DNA. SEQ ID 12 contains a bacteriophage T7 RNA polymerase promoter followed by the sequence corresponding to the signal tag derived from the D domain of *L. tropica*. SEQ ID 13 and 14 contain a sequence complementary to part of the signal tag. Thus when the two ODNs hybridize to each other, a partially double-stranded molecule is formed.
(2) The partially double-stranded intermediate is converted to the fully double stranded form by gap-filling with the Klenow fragment of *E. coli* DNA polymerase I. This forms the promoter-tag cassette. The promoter-tag cassettes consists of a T7 RNA polymerase promoter immediately upstream of the signal tag oligonucleotide sequence.

(3) The cassette is flanked by restriction sites for Eco RI and Barn HI (or for Eco RI and Hind III). Cleavage with these enzymes liberates cohesive ends with 5'-phosphate groups.

(4) The terminal phosphate groups are removed with alkaline phosphatase to prevent self-ligation of the cassette in the next step.

(5) The protein coding sequences to be tagged are amplified from human mitochondrial DNA (isolated from cell line HepG2) by polymerase chain reaction (PCR) using the appropriate primer pairs (TABLE 3; SEQ ID 15-20).

(6) The amplified protein coding fragment is digested with the appropriate restriction enzymes to liberate cohesive ends.

(7) Each amplified protein-coding DNA is attached to the promoter tag cassette with DNA ligase.

(8) The ligation product is amplified by PCR using flanking primers (TABLE) to generate the transcription template containing the T7 promoter, the signal tag followed by the protein-coding sequence. The transcription template can be stored in aliquots at −20° C.

(9) The template is transcribed in vitro with T7 RNA polymerase to yields the full-length tagged pcRNA.

(10) The RNA is recovered by ethanol precipitation, suspended in water, aliquoted, lyophilized, and stored at −70° C. (component B).

For each of first six steps, were performed using standard recombinant DNA techniques which involve enzymatic manipulations. The materials (enzymes, oligonucleotides) are available commercially. Standard published procedures are performed and scaled up as necessary (pmol to μmol scale).

It is also possible, in principle, to chemically synthesize signal tagged pcRNA, or to chemically modify/replace the phosphodiester backbone, sugar moieties or bases, in order to improve the in vivo stability or target recognition of the RNA or DNA. There is abundant prior art on these modifications and their applications. Any such modification to signal tagged pcRNAs is not considered to alter the basic principle of carrier mediated transfer, and thus falls within the ambit of the invention.

Composition of Binding Buffer:

An aqueous solution of Tris-HCl, 20 mmol/li; $MgCl_2$, 20 mmol/li; dithiothreitol, 2 mol/li; NaCl, 200 mmol/li; glycerol, 10%. Total volume: 10 μL.

Formation of the RNP Complex

Prior to administration, (1) the lyophilized RNA (component B) is reconstituted with binding buffer.

(2) The carrier complex (component A) is thawed on ice.

(3) Component A is added to reconstituted component B and the mixture is incubated on ice for 30 min to form the RNP complex. A typical RNP preparation consists of an aqueous solution of pcRNA 1-3, 1 pmol each; R8, 0.16 μg/ml; Tris-HCl, 10 mmol/li; $MgCl_2$, 10 mmol/li; dithio threitol, 1 mol/li; NaCl, 100 mmol/li; glycerol, 10%. Total volume: 20 μL.

TABLE 3

Oligonucleotide Primers

| Primer | PCR product | ODN No (HCR | Sequence id | Content | Orientation S/AS | Sequence |
|---|---|---|---|---|---|---|
| 1 | Promoter-tag cassette (pcRNA 1,2) | O-43 | 12 | T7 promoter, signal tag | S | GGAATTCTAATACGACTCACTATAGGGACTGTAGCTC |
| | | O-307 | 13 | Signal tag | AS | GGGATCCATGCTCTACCAATTGAGCTACAGTC |
| 2 | Promoter-tag cassette (pcRNA 3) | O-43 | 12 | T7 promoter, signal tag | S | GGAATTCTAATACGACTCACTATAGGGACTGTAGCTC |
| | | O-298 | 14 | Signal tag | AS | GAAGCTTATGCTCTACCAATTGAGCTACAGTC |
| 3 | pcRNA-1 | O-247 | 15 | COI 5' coding | S | GCGGATCCATGTTCGCCGACCGTT |
| | | O-256 | 16 | COIII 3' coding | AS | GCGAATTCAAGACCCTCATCAATAGAT |
| 4 | pcRNA-2 | O-255 | 17 | COIII coding 5' | S | GCGGATCCATGACCCACCAATCAC |
| | | O-263 | 18 | CYB coding 3' | AS | ATCGATCGAGGCCCATTTGAGTAT |
| 5 | pcRNA-3 | O-243 | 19 | ND1 coding 5' | S | GCAAGCTTATACCCATGGCCAACC |
| | | O-248 | 20 | COI coding 3' | AS | GCGCGGATCCTCTAGATTTTATG |

(4) The RNP is diluted into sterile phosphate buffered saline, or equivalent buffer, or culture medium, to a concentration of 1 pmol (of each RNA)/ml.

For optimization, the RNA concentration is varied between 0.1 and 10 pmol/ml and the carrier between 0.1-1 μg/ml. Optimization is important since a sharp threshold (at ~1 pmol/ml of RNA) is observed in cell culture assays.

In the invention, the formulation is in aqueous medium for the purpose of injection. It is possible to make other preparations involving different bases, e.g., water or oil-based ointments, gels, creams, suppositories, etc. for topical applications. It may also be possible in future to develop formulations for oral administration. The biological activity of all such formulations and routes of administration being dependent on the presence of pcRNAs and specific carrier complexes as defined above, these alternative formulations and roots of administration fall within the purview of this invention.

Facile Uptake and Mitochondrial Targeting.

Figure 9:
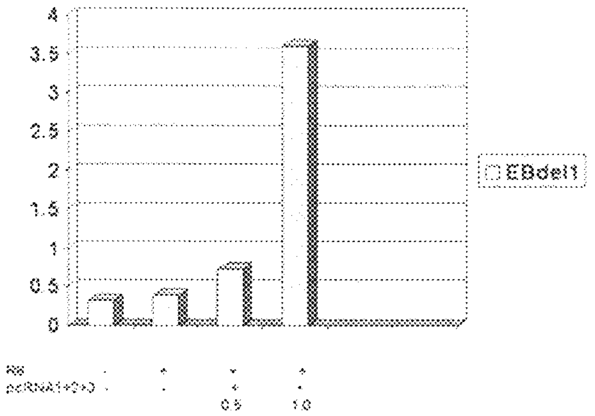
FIG. 9 is a representation of the uptake of Alexa fluor 488-labeled pcRNA-1 (green) by Retinal Pigment Epithelial cells. Mitochondria within live cells were counter stained with MitoTracker Deep red 633 (red).
Figure 10:
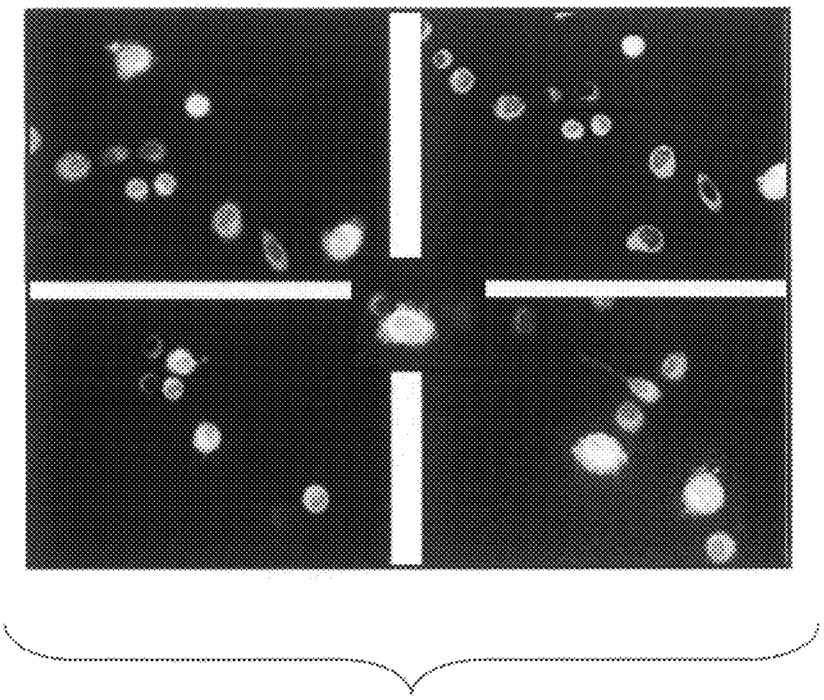
FIG. 10 is a representation of the uptake of Alexa fluor 488-labeled pcRNA-1 (green) by rat skeletal muscle. Longitudinal sections (10 μm) in proximo-distal orientation relative to the injection site (s1-s3) counterstained with MitoTracker 633 (red). A male rat was injected in the left hind limb gastrocnemius muscle with 1 pmol of pcRNA-1 labeled with Alexa fluor 488-UTP. After 24 h, cryosections of the muscle biopsy was counterstained with MitoTracker 633.
Figure 11:
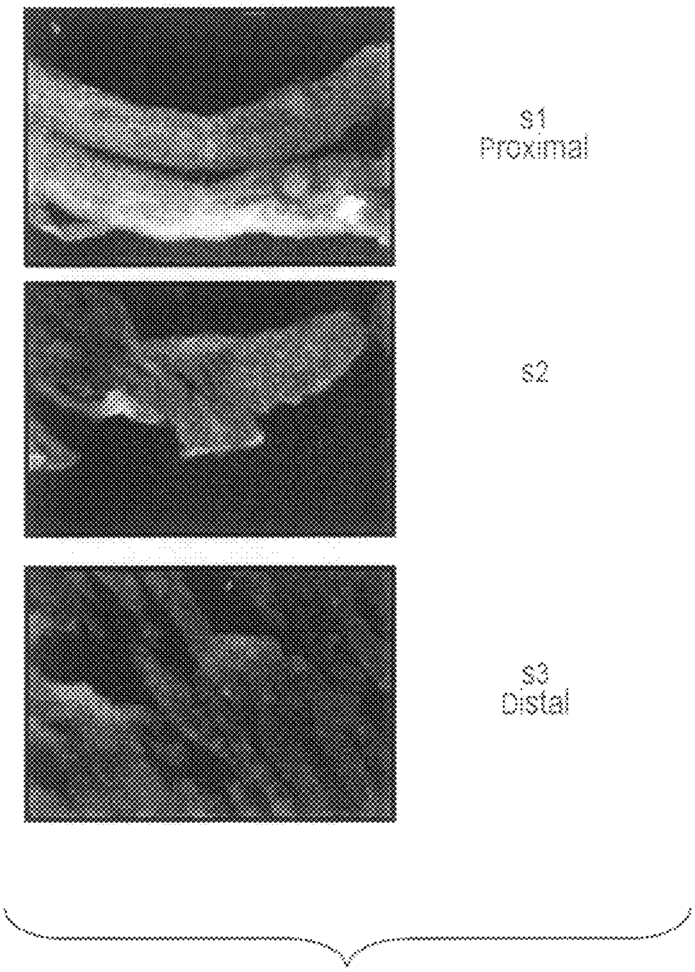
FIG. 11. is a graphical representation of the walk speed of aged rats treated with pcRNA1, 2, and 3 plus R8. Animals 1, 2, and 5 were injected on both hind limbs with the combination. Animal 4 received control RNA. Walk speed of each animal (color coded as shown in the legend) representing the average of 3-5 independent runs up an incline of 45°, was measured at the times indicated. The trendline for animal 2 is shown.

The native carrier complex, or R8, or RNA complexed with it, has been shown to be taken up in a wide variety of cell types, including hepatocarcinoma, osteosarcoma-derived cybrid lines, primary cardiomyocytes [Mahata B., Mukherjee, S., Mishra, S., Bandyopadhyay, A., & Adhya, S. (2006) Functional delivery of a cytosolic tRNA into mutant mitochondria of human cells. *Science.* 314: 471-474], retinal pigment epithelial cells [FIG. 9], and into skeletal muscle in vivo [FIG. 10]. In each case, the carrier or the cargo RNA has been observed to be localized to mitochondria. The cell lines are of human origin, and rats are standard animal models with organ systems, including skeletal muscle, that are very similar to those of humans.

1) Rescue of respiration of cells bearing a mitochondrial tRNA mutation by the carrier complex.
2) Phenotypic correction of mitochondrial mutation derived from Kearns-Sayre Syndrome by the R8-pcRNA-1 complex.
3) Rescue of multiple mitochondrial deletions by a combination of pcRNAs 1, 2 and 3: cooperative and threshold effects.
4) Threshold effect on respiration rescue by pcRNA formulation.
5) Uptake of carrier by primary and cultured cells.
6) Uptake of pcRNA by rat skeletal muscle in vivo.
7) Stimulation of performance of aged rats in walk test by pcRNA formulation.

Facile Uptake and Mitochondrial Targeting.

The native carrier complex, or R8, or RNA complexed with it, has been shown to be taken up in a wide variety of cell types, including hepatocarcinoma, osteosarcoma-derived cybrid lines, primary cardiomyocytes [Mahata B., Mukherjee, S., Mishra, S., Bandyopadhyay, A., & Adhya, S. (2006) Functional delivery of a cytosolic tRNA into mutant mitochondria of human cells. *Science.* 314: 471-474], retinal pigment epithelial cells [FIG. 9], and into skeletal muscle in vivo [FIG. 10]. In each case, the carrier or the cargo RNA has been observed to be localized to mitochondria. The cell lines are of human origin, and rats are standard animal models with organ systems, including skeletal muscle, that are very similar to those of humans.

Thus, the carrier mediated delivery method of the invention is expected to be applicable to a wide variety of cells, tissues and organs of human subjects.

Rescue of Mitochondrial tRNA Point Mutations.

The native form of the carrier complex [Mahata B., Mukherjee, S., Mishra, S., Bandyopadhyay, A., & Adhya, S. (2006) Functional delivery of a cytosolic tRNA into mutant mitochondria of human cells. *Science.* 314: 471-474], or R6 or R8, restores respiration in cells harboring the A8344G mutation in the mitochondrial tRNAlys gene, by inducing the import of functional tRNALys from the cytosol. This mutation occurs in many mitochondrial diseases including Myoclonic Epilepsy with Ragged Red Fibers (MERRF); Leigh Syndrome; Parkinson syndrome, Neuropathy and Myopathy; and Multiple Symmetric Lipomatosis. Other mutations in the same gene are associated with Cardiomyopathy (G8363A); Progressive External Opthalmoplegia (PEO) with Monoclonus (G8342A); and Maternally Inherited Diabetes, with Deafness (MIDD) (A8296G). [Neuromuscular Disease Center, Washington University, St. Louis, Mo. USA. Mitochondrial Disorders.

Moreover, the carrier complex has broad tRNA specificity, and in human cells it induces the import of many other cytosolic tRNAs [Mukherjee, S., Basu, S., Home, P., Dhar, G., & Adhya, S. (2007) Necessary and sufficient factors for import of tRNA into the kinetoplast-mitochondrion. *EMBO Rep.,* 8: 589-595], the corresponding mitochondrial tRNAs of which are mutated in various mitochondrial disorders. These include (1) tRNALeu mutations associated with Mitochondrial Encephalopathy, Lactic Acidosis and Stroke (MELAS); Riboflavin sensitive myopathy; Isolated cardiomyopathy; Maternally Inherited Diabetes, with Deafness (MIDD); Sudden Infant Death syndrome (SIDS); Maternal Deafness, whether or not syndromic [Neuromuscular Disease Center, Washington University, St. Louis, Mo. USA. Mitochondrial Disorders. (2) tRNAGln mutations in Late Onset Alzheimer's Disease [Hutchin, T. & Cortopassi, G. (1995) *Proc. Natl. Acad. Sci. U.S.A.* 92: 6892]. (3) tRNAIle mutation in Metabolic Syndrome.

Thus the invention is suitable for the treatment of the above disorders, and of any others caused by point mutations in mitochondrial tRNA genes.

Rescue of Point Mutations in Mitochondrial Protein-Coding Genes.

The invention provides an efficient method for delivery of pcRNAs encoding full-length genes with normal (wild-type) sequence. Delivery of all of the protein-coding genes except ND6 can be achieved by the invention [FIG. 3] [TABLE 2].

TABLE 2

Identities of pcRNA-1, 2, and 3.

| | | | | Mt protein-coding genes | | Other mt genes | |
|---|---|---|---|---|---|---|---|
| Name | Sequence id | Length (bases) | Signal tag | Identity | Position | Identity | Postiton |
| pcRNA-1 | 9 | 4112 | D arm of tRNATyr, 5'-end | COI | 5904-7445 | tRNASer | 7445-7516 |
| | | | | COII | 7586-8269 | tRNAAsp | 7518-7585 |
| | | | | ATP8 | 8366-8572 | tRNALys | 8295-8364 |
| | | | | ATP6 | 8527-9207 | | |
| | | | | COIII | 9207-9987 | | |

TABLE 2-continued

Identities of pcRNA-1, 2, and 3.

| Name | Sequence id | Length (bases) | Signal tag | Mt protein-coding genes Identity | Position | Other mt genes Identity | Postiton |
|---|---|---|---|---|---|---|---|
| pcRNA-2 | 10 | 6704 | D arm of tRNATyr, 5'-end | COIII | 9207-9987 | tRNAGly | 9991-10058 |
| | | | | ND3 | 10059-10404 | tRNAArg | 10405-10469 |
| | | | | ND4L | 10470-10766 | tRNAHis | 12138-12206 |
| | | | | ND4 | 10760-12137 | tRNASer | 12207-12265 |
| | | | | ND5 | 12337-14148 | tRNALeu | 12266-12336 |
| | | | | CYTB | 14747-15881 | | |
| pcRNA-3 | 11 | 4107 | D arm of tRNATyr, 5'-end | ND1 | 3307-4263 | tRNAIle | 4263-4331 |
| | | | | ND2 | 4470-5511 | tRNAGln | 4329-4000 |
| | | | | CO I | 5904-7445 | tRNAMet | 4402-4469 |
| | | | | | | tRNATrp | 5512-5579 |
| | | | | | | tRNAAla | 5587-5655 |
| | | | | | | tRNAAsn | 5657-5729 |
| | | | | | | tRNACys | 5761-5826 |
| | | | | | | tRNATyr | 5826-5891 |

Many mitochondrial disorders are associated with point mutations in mitochondrial protein-coding genes. These include: Neuropathy, Ataxia, and Retinitis Pigmentosa [NARP] (ATP6); Leber's Hereditary Optic Neuropathy (LHON) (ND4, ND 1); Myopathy, Exercise Intolerance, Encephalopathy, Lactic Acidemia (COIII); and others [Neuromuscular Disease Center, Washington University, St. Louis, Mo. USA. Mitochondrial Disorders.

In these cases, identification of the point mutation will allow the formulation of the invention to be tailor-made accordingly. For example, delivery of pcRNA-1, encoding ATP6, may be used to treat NARP.

Thus, the invention is suitable for the treatment of the above disorders, and of any others caused by point mutations in mitochondrial protein-coding genes.

Rescue of Deletions in Mitochondrial DNA.

The invention provides an efficient method for transferring large RNAs containing multiple protein-coding sequences. Many mitochondrial disorders are associated with mitochondrial DNA deletions. These include: Kearns-Sayre Syndrome (KSS); maternal or sporadic syndromic deafness; Pearson's Syndrome; Sideroblastic Anemia; Wolfram Syndrome (Diabetes Insipidus, Diabetes Mellitus, Optic Atrophy, Deafness or DIDMOAD); Myopathy and external opthalmoplegia, Neuropathy, Gastro-Intestinal and Encephalopathy (MNGIE); Inclusion Body Myositis; polymyositis with $COX^-$ muscle fibers. Mitochondrial deletions also accumulate in conditions not diagnosed as a clinical disorder, most notably, aging.

Figure 7:
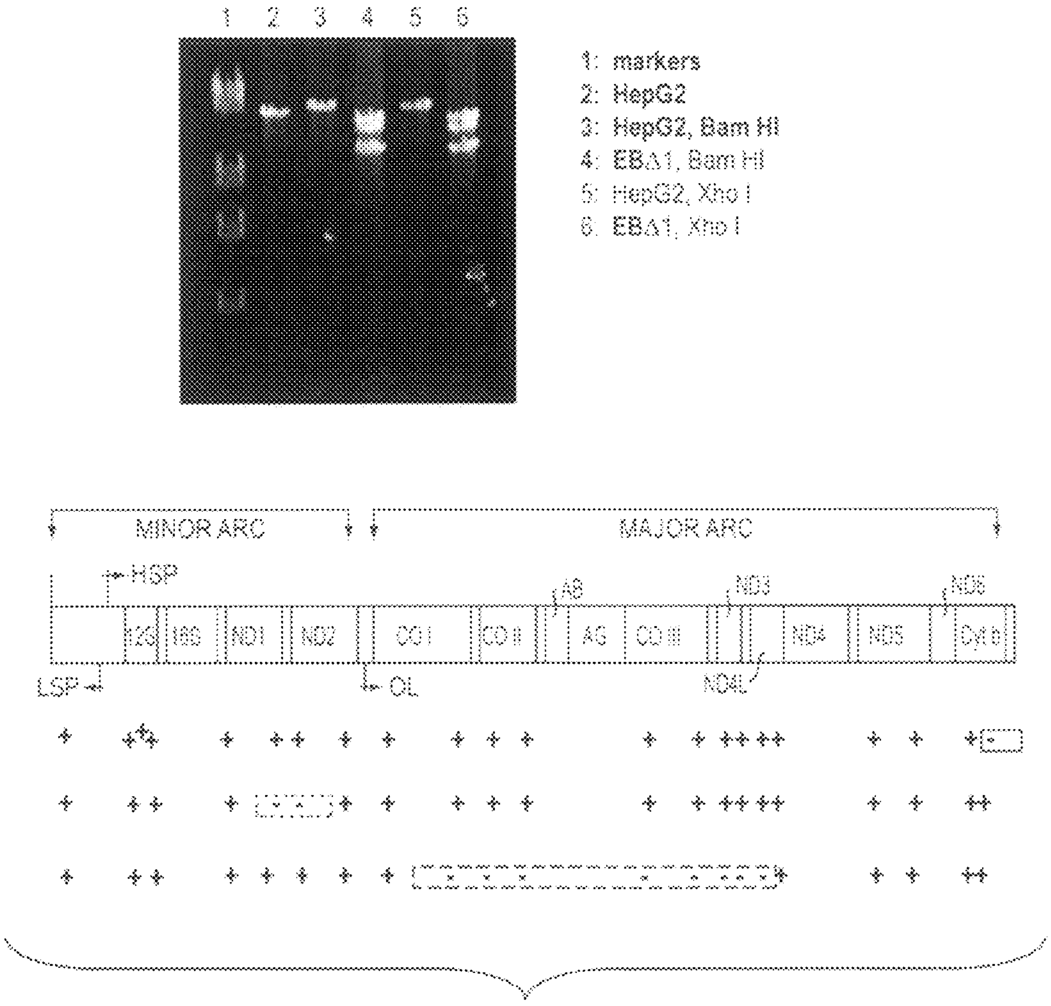
FIG. 7 is a representation of the effect of pcRNA combination on rescue of respiration of EBΔ1. 1-2×10e6 cells were cultured in presence of R8 and indicated combinations of pcRNA 1, 2, and 3, for 5 d, then their $O_2$ uptake was measured.

By providing large pcRNAs with near genome-wide coverage, the invention rescues respiration in cells containing single [FIG. 5] or multiple [FIG. 7] mitochondrial deletions.

Thus, the invention is suitable for the treatment of mitochondrial disorders including aging, and of any others caused by deletions of mitochondrial protein-coding genes.

Statement of Novelty

The novel features of the present invention are

1) It delivers large RNAs of many kilobases length, while the prior art describes the delivery of short RNAs (~40 bases).
2) The pcRNAs of this invention have protein-coding sequences which, upon expression within mitochondria, are translated to functional proteins.
3) pcRNAs stimulate respiration in cells bearing mitochondrial deletions.
4) A combination of pcRNAs with genome-wide coverage of protein-coding sequences is used to correct genetic defects.
5) It employs functional carrier complexes R6 and R8 which are expressed in bacteria and assembled in vitro.

WORKING EXAMPLES

The following working examples are provided to demonstrate preferred embodiments of the invention, but of course, should not be construed as in any way limiting the scope of the present invention. The examples below were carried out using conventional techniques that are well known and routine to those of skill in the art, except where otherwise described in detail. Further, it should be appreciated by those of skill in the art that the techniques disclosed in the examples represent techniques found by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All animal experiments were carried out according to Institutional ethical guidelines.

Example 1

Rescue of Respiration of Cells Bearing a Mitochondrial tRNA Mutation by the Carrier Complex The bio-assay of carrier complexes uses the cytoplasmic hybrid (cybrid) cell line (LB64) that is nearly homoplasmic for the mitochondrial mutation A8344G mutation in the tRNAlys gene derived from a patient with Myoclonic Epilepsy with Ragged Red Fibers (MERRF). [Masucci, J. P., Davidson, M., Koga, Y., Schon, E., and King, M. P. (1995) *Mol. Cell. Biol.* 15: 2872-2881] Cells (1×10e6) were cultured in DMEM medium containing 10% fetal bovine serum in presence of R6, R8 or native form (0.16-2 μg/ml) for 5 d, then harvested and their $O_2$ uptake rate in phosphate buffered saline (PBS) containing 2 mM glucose was recorded by a Clarke-type oxygen electrode (YSI Instruments).

In the absence of carrier, LB64 has low respiration rate, due to the mutation which affects mitochondrial protein synthesis

[FIG. 5]. Each carrier complex restored respiration to ~75%. In this case, rescue of respiration is due to uptake and targeting of the complex to mitochondria in an active form that induces transport of cytosolic tRNAs (including tRNALys) that complement the tRNA mutation. This experiment demonstrates the ability of all the carrier complexes to be translocated in an active form to intracellular mitochondria where they the induce the import of cytosolic tRNAs.

Example 2

Phenotypic Correction of Mitochondrial Mutation Derived from Kearns-Sayre Syndrome by the R8-pcRNA-1 Complex The cybrid line FLP32.39 is nearly homoplasmic for a 1.9-kb deletion of mitochondrial DNA derived from a patient with Kearns-Sayre syndrome, a progressive multi-organ disorder characterized by progressive external opthalmoplegia (PEO), myopathy, sensorineural defects, heart block, lactic acidosis and other symptoms. The mitochondrial DNA in these cells lacks the COII, COIII, ATP6 and ATP8 protein-coding genes, as well as the single mitochondrial tRNALys gene, and is therefore respiratory deficient. The rate of $O_2$ uptake by FLP32.39 is less than 10% of the hepatocarcinoma cell line HepG2 containing wild-type mitochondria [FIG. 6].

Figure 6:
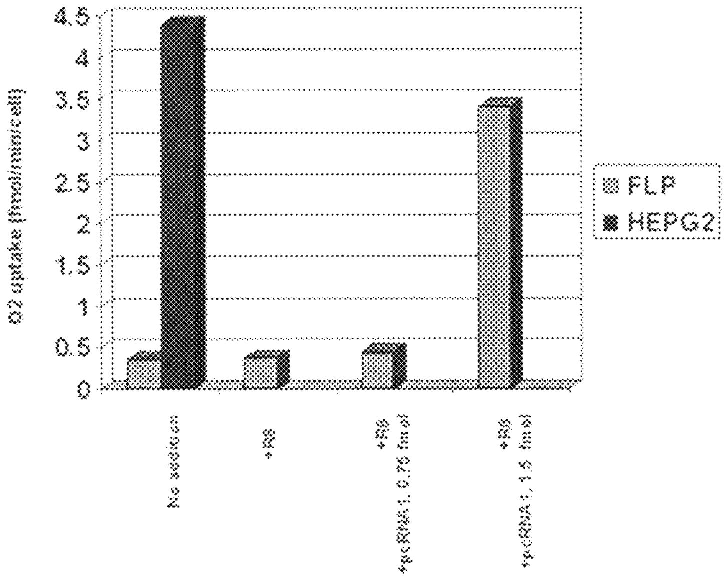
FIG. 6 is a plot of Oxygen uptake of FLP32.39 cells treated with pcRNA1+R8. The effect of signal-tagged pcRNA-1-R8 combination on respiration of cybrid FLP32.39 carrying a 1.9-kb mitochondrial deletion.

FLP32.39 cells (1.4×10e6 cells on a monolayer) were cultured with 0.75 or 1.5 pmol/ml signal-tagged pcRNA-1 [SEQ ID 9] combined with 0.16 μg/ml R8 in DMEM medium containing 10% fetal bovine serum for 5 days [FIG. 6] The carrier alone had no effect on cellular respiration, but in presence of 1.5 pmol/ml signal tagged Pc RNA-I, respiration was restored to ~75% of normal (FIG. 2 FIG. 5). At a two-fold lower RNA concentration (0.75 pmol/ml) there was no significant effect; saturation was achieved above 1 pmol/ml. Thus, pcRNA-1 restores respiration in the KSS mitochondria, and shows a threshold effect.

Due to the threshold effect it is important for maximum efficacy to optimize the dose for each clinical situation.

Example 3

Rescue of Multiple Mitochondrial Deletions by a Combination of pcRNAs 1, 2 and 3: Cooperative Effects Many mitochondrial disorders are associated with the occurrence of single deletions of mitochondrial DNA, but the extent and map position of the deletions vary between patients. In aged animal and human subjects, mitochondrial deletions are detected in various post-mitotic tissues including skeletal muscle, and substantia nigra (brain). The deletions expand clonally in different regions of the tissue. Multiple deletions within the same aged subject have also been detected. The proposed formulation of pcRNA-1, 2 and 3 and R6/R8 is able to rescue respiration of a population of cells containing multiple mitochondrial deletions.

In the cell line EBΔ1, a derivative of HepG2 (human hepatocarcinoma, wild-type mitochondrial DNA), multiple mitochondrial genomes are observed, with the deletions mapping to different parts of the genome [FIG. 7].

Monolayer cultures of EBΔ1 (1.1-1.76×10e6 cells) were treated with 1 pmol/ml of pcRNA in various combinations and 0.16 μg/ml R8 in DMEM medium containing 10% fetal bovine serum at 37° C. under 5 $CO_2$ for 5 days. The $O_2$ consumption of the cells was measured.

Figure 8:
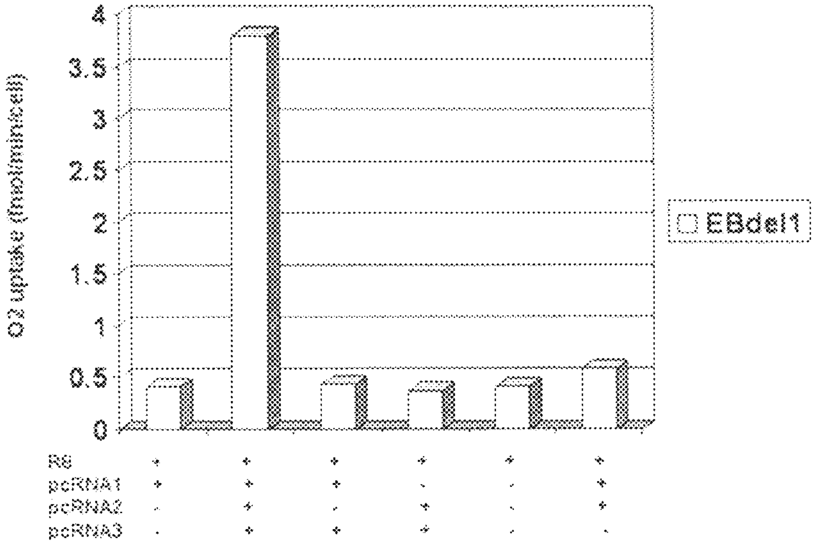
FIG. 8 is a representation of the effect of RNA concentration on respiration of EBΔ1.

This experiment shows that only a combination of all 3 pcRNAs is competent to rescue the respiration defect caused by multiple mitochondrial deletions [FIG. 8].

Example 4

Threshold Effect on Respiration Rescue by pcRNA Formulation

EBΔ1 cells (1.2-1.9×10e6) were cultured as in example 3 with the pcRNA 1-3 combination (0.5 or 1 pmol each/ml) and R8 (0.16 μg/ml) for 5 days, and $O_2$ uptake measured as before. Below 1 pmol/ml RNA concentration, there is hardly any effect, demonstrating a clear threshold [FIG. 9].

Example 5

Uptake of pcRNA-1 by Retinal Pigment Epithelial Cells In Vitro

Retinal pigment epithelial (RPE) cells were cultured on a poly-L-lysine coated slide, and incubated with Alexa Fluor 488-labeled pcRNA-1 (1 pmol/ml) plus R8 (0.16 μg/ml) for 24 h. Live cells were counterstained with MitoTracker Deep red 633, a mitochondrial marker, and imaged with a fluorescence microscope (Nikon Eclipse 200, triple band excitation filter, 400×).

The RNA (green) was observed to have been taken up by most cells, although there is variability in the fluorescence intensity between cells. Within the cells, the fluorescence colocalized with mitochondria (stained red by MitoTracker). The resultant fluorescence thus varied from orange to yellow [FIG. 10]

Example 5

Uptake of pcRNA1 by Rat Skeletal Muscle In Vivo

Male adult rats were injected intramuscularly (hind limb gastrocnemius) with 1 pmol of pcRNA1, labeled with the fluorophor Alexa Fluor 488 [REF], in ~0.1 ml sterile phosphate buffered saline (PBS). After 24 h, muscle biopsy specimens from the vicinity of the injection site were counterstained with Mitotracker Deep Red 633, a mitochondrial marker, and examined under a fluorescence microscope (Nikon Eclipse 200, triple band excitation filter, 40×). High concentrations of RNA (green) were observed in the proximal sections, with a gradient of decreasing concentrations in more distal sections [FIG. 10]. (N.B. Decrease of green emission. i.e. green: red ratio, results in changes in the mixed color from green to red).

Large signal-tagged pcRNAs, such as pcRNA-1, injected intramuscularly along with carrier into rats, are present in individual muscle fibers within 24 h, diffusing from the injection site down the length of the fibers. Since prior art demonstrates that human and rat skeletal muscle have very similar structure and contractile properties, it is predicted that pcRNAs will be similarly transported within the skeletal muscle of human subjects.

Example 6

Effect of pcRNA Formulation on Performance of Aged Rats in Walk Test

The therapeutic efficacy of the pcRNA combination was tested in an aged rat model. Individual animals (male, 1.5 yr) were made to perform a walk test.

Figure 12:
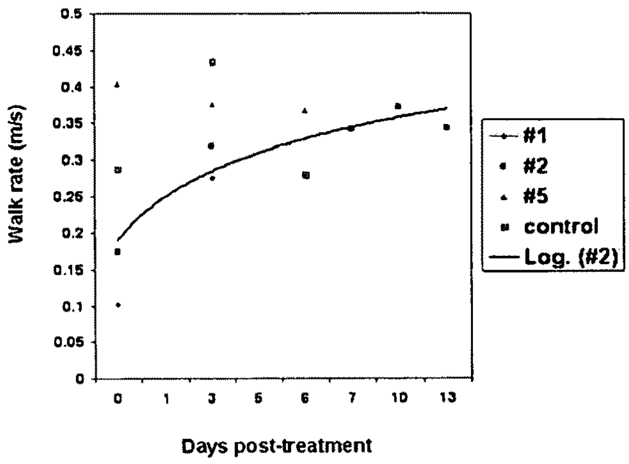
FIG. 12 is a graph of walk speed of aged rats treated with pcRNA1, 2, and 3 plus R8. Animals 1, 2, and 5 were injected on both hind limbs with the combination. Animal 4 received control RNA. Walk speed of each animal representing the average of 3-5 independent runs up an incline of 45°, was measured at the times indicated. The trend line for animal 2 is shown.

The walk test consists of making the animal walk 1 m up an incline of 45° towards a dark chamber, during which time a number of parameters may be monitored through footprint analysis, e.g., slide length, foot length, toe spread, etc. [Klapdor, K., et al. (1997) *J. Neurosci. Meth.* 78: 49] Another parameter that is a measure of the animal's performance is walk speed, defined hereinafter as inverse of the time (in sec) taken by the animal to walk 1 m up the incline of 45°. Each animal was pre-acclimatized to the test conditions the day before the measurement. The subject was made to walk up the incline 3-5 times and each run was timed. Young subjects (3 mo, male, 130-150 g) ran up faster (walk speed 0.5-0.7 m/s) than the older subjects (1.5 yr, male, 250-275 g), as expected, but there was variability (0.1-0.4 m/s) within the aged group [FIG. 12].

Old rats were injected in the gastrocnemius muscle of each limb with pcRNA1-3 (1 pmol each) combined with 0.16 μg of R8, or with a control RNA (containing only the signal tag but no protein-coding sequences) combined with 0.16 μg of R8. Subjects that were initially poor performers (walk speed 0.1-0.2 m/s) showed significant improvement after 3 days of administration of the formulation, going up to 0.3-0.4 m/s [FIG. 12]. The enhanced speed was maintained for at least 2 weeks. If the aged subject (e.g. animal #5) was already a good performer (walk speed 0.4 m/s), the pcRNA caused no further improvement. In summary, it was observed that the performance of two out of three aged animals (both poor performers to start with) was significantly improved by administration of the pcRNA combination with carrier. This indicates that the formulation will find application in improving the performance of the skeletal muscle of aged subjects; subjects with myopathy or exercise intolerance; and patients with mitochondrial disease indicated by the presence of deletions, rearrangements or point mutations in mitochondrial DNA.

All publications, patents and patent applications mentioned in the specification are indicative of the level of those skilled in the art to which this invention pertains. All publications, patents and patent applications are herein incorporated by reference to the same extent as if each individual publication or patent application was specifically and individually indicated to be incorporated by reference.

The foregoing specification teaches the principles of the present invention, with description of the preferred embodiments, and with examples provided for the purpose of illustration, so as to enable any person skilled in the art to make and use the present invention. The various modifications to these embodiments will be readily apparent to those skilled in the art, and the generic principles defined herein may be applied to other embodiments without the use of the inventive faculty. Thus, the present invention is not intended to be limited to the embodiments shown herein but is to be accorded the widest scope consistent with the principles and novel features disclosed herein and the following claims and its equivalents.

I claim:

1. A recombinant polyribonucleotide segment comprising the full sequence of SEQ ID NO:9, the full sequence of SEQ ID NO:10 or the full sequence of SEQ ID NO:11, wherein the full sequence comprises an operably linked signal tag.

2. The recombinant polyribonucleotide segment of claim 1, wherein the full sequence is the full sequence of SEQ ID NO: 9.

3. The recombinant polyribonucleotide segment of claim 1, wherein the full sequence is the full sequence of SEQ ID NO: 10.

4. The recombinant polyribonucleotide segment of claim 1, wherein the full sequence is the full sequence of SEQ ID NO: 11.

5. A composition comprising the full sequence of SEQ ID NO:9, the full sequence of SEQ ID NO:10 or the full sequence of SEQ ID NO:11 or a mixture thereof.

6. The composition of claim 5, wherein the composition comprises the full sequence of SEQ ID NO:9, the full sequence of SEQ ID NO:10 and the full sequence of SEQ ID NO:11.

7. The composition of claim 5, further comprising a binding buffer.

8. A composition comprising an amount of the full sequence of SEQ ID NO:9, the full sequence of SEQ ID NO:10 or the full sequence of SEQ ID NO:11 or a mixture thereof, a carrier comprising a group of proteins comprising SEQ ID NOS: 1, 3, 5, 6, 7 and 8 and a binding buffer.

9. A diagnostic kit for screening mitochondrial dysfunction in a patient sample comprising:

a carrier (component A), wherein the carrier is R6 (SEQ ID NOS: 1, 3, 5, 6, 7 and 8) and/or R8 (SEQ ID NOS: 1-8), a pc RNA (protein-coding RNA) (component B), wherein the pc RNA is a recombinant polyribonucleotide segment comprising the full sequence of SEQ ID NO:9, the full sequence of SEQ ID NO:10 or the full sequence of SEQ ID NO:11, a binding buffer, and an instruction manual for carrying out diagnosis.

* * * * *

UNITED STATES PATENT AND TRADEMARK OFFICE

CERTIFICATE OF CORRECTION

PATENT NO. : 9,127,080 B2
APPLICATION NO. : 12/584059
DATED : September 8, 2015
INVENTOR(S) : Adhya It is certified that error appears in the above-identified patent and that said Letters Patent is hereby corrected as shown below:

Title Page:

Insert the following:

-- (30) Foreign Application Priority Data
August 28, 2008 (IN) ................ 2034/DEL/2008 --

Signed and Sealed this
Seventh Day of June, 2016

Michelle K. Lee
*Director of the United States Patent and Trademark Office*